United States Patent [19]
Freeman et al.

[11] Patent Number: 5,942,607
[45] Date of Patent: Aug. 24, 1999

[54] B7-2: A CTLA4/CD28 LIGAND

[75] Inventors: Gordon J. Freeman, Brookline; Lee M. Nadler, Newton; Gary S. Gray, Brookline, all of Mass.

[73] Assignee: Dana-Farber Cancer Institute, Boston, Mass.

[21] Appl. No.: 08/101,624

[22] Filed: Jul. 26, 1993

[51] Int. Cl.⁶ .................. C07H 21/00; C07K 14/705; C12N 15/12
[52] U.S. Cl. ................ 536/23.5; 530/350; 935/9
[58] Field of Search .................. 536/23.5; 530/350; 435/69.3, 240.1–240.2, 252.3, 320.1, 325; 514/12; 935/9

[56] References Cited

PUBLICATIONS

D.J. Lenschow et al PNAS 90:11054–8 Dec. 1, 1993.
V.A. Boussiotis et al. PNAS 90:11059–63 Dec. 1, 1993.
G.J. Freeman et al. Science 262:909 Nov. 5, 1993.
S.O. Southern et al. J. Immunol. 142:336–342 Jan. 1, 1989.
Schwartz, "A Cell Culture Model for Lymphocyte Clonal Anergy" *Science*, vol. 248, pp. 1349–1356, (1990).
Reiser et al., "Murine B7 antigen provides an efficient costimulatory signal activation of murine T lymphocytes via T cell receptor/CD3 complex" *Proceedings of the National Academy of Sciences*, vol. 89, pp. 271–275, (1992).
Freeman et al., "Structure, Expression, and T Cell Costimulatory Activity of the Murine Homologue of the Human B Lymphocyte Activation Antigen B7" *Journal Experimental Medicine*, vol. 174, pp. 625–631, (1991).
Gimmi et al., "B–cell surface antigen B7 provides a costimulatory signal that induces T cells to proliferate and secrete interleukin 2" *Proceedings of the National Academy of Sciences*, vol. 88, pp. 6575–6579, (1991).
Linsley et al., "Binding of the B Cell Activation Antigen B7 to CD28 Costimulates T Cell Proliferation and Interleukin 2 mRNA Accumulation" *Journal Experimental Medicine*, vol. 173, pp. 721–730, (1991).
Freeman et al., "B7, A New Member of the Ig Superfamily with Unique Expression on Activated and Neoplastic B Cells" *Journal of Immunology*, vol. 143, No. 8, pp 2714–2722, (1989).
Thompson et al., "CD28 activation pathway regulates the production of multiple T–cell derived lymphokines/cytokines" *Proceedings of the National Academy of Sciences*, vol. 86, pp. 1333–1337, (1989).
Freedman et al., "B7, A B Cell–Restricted Antigen That Identifies Preactivated B Cells" *Journal of Immunology*, vol. 139, No. 10, pp. 3260–3267, (1987).

*Primary Examiner*—Lorraine Spector
*Attorney, Agent, or Firm*—Lahive & Cockfield, LLP; Amy E. Mandragouras; Megan E. Williams

[57] ABSTRACT

Isolated nucleic acids encoding novel CTLA4/CD28 ligands which costimulate T cell activation are disclosed. In one embodiment, the isolated nucleic acid has a sequence which encodes a B lymphocyte activation antigen, B7-2. Preferably, the nucleic acid is a DNA molecule comprising at least a portion of a nucleotide sequence shown in FIG. 8, SEQ ID NO: 1. The nucleic acid sequences of the invention can be integrated into various expression vectors, which in turn can direct the synthesis of the corresponding proteins or peptides in a variety of hosts, particularly eukaryotic cells, such as mammalian and insect cell culture. Also disclosed are host cells transformed to produce proteins or peptides encoded by the nucleic acid sequences of the invention and isolated proteins and peptides which comprise at least a portion of a novel B lymphocyte antigen.

9 Claims, 18 Drawing Sheets

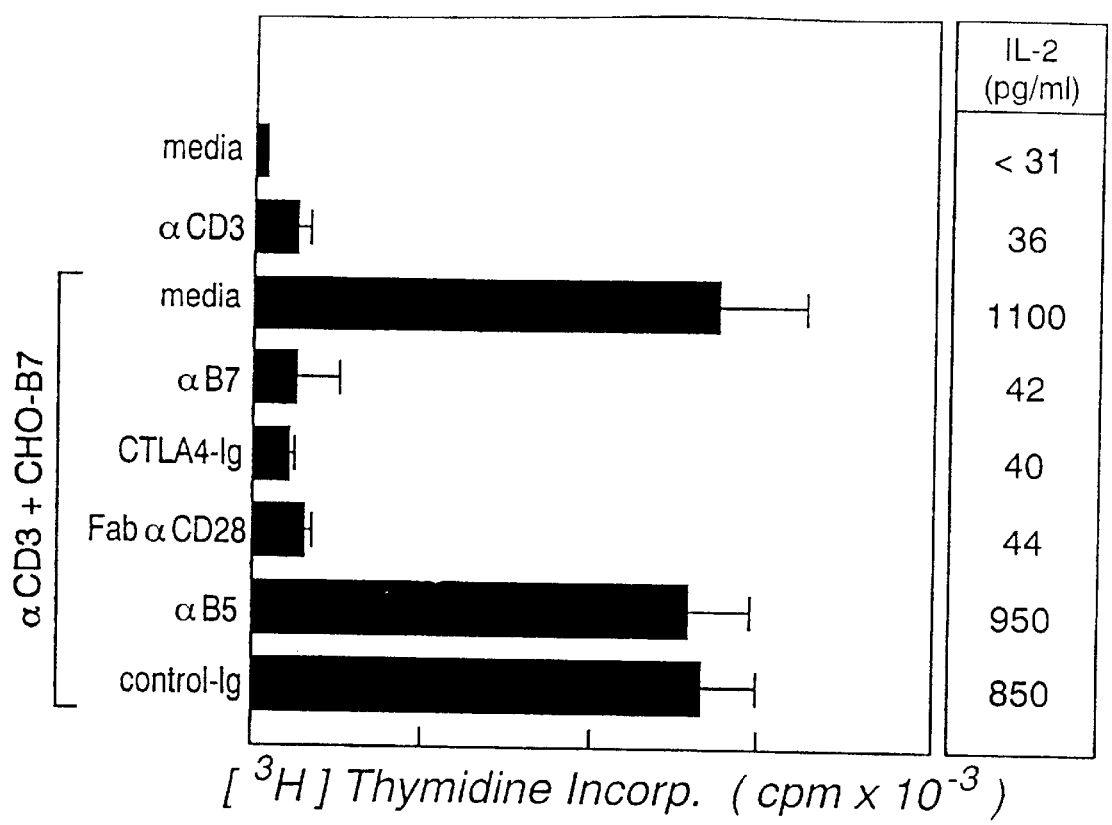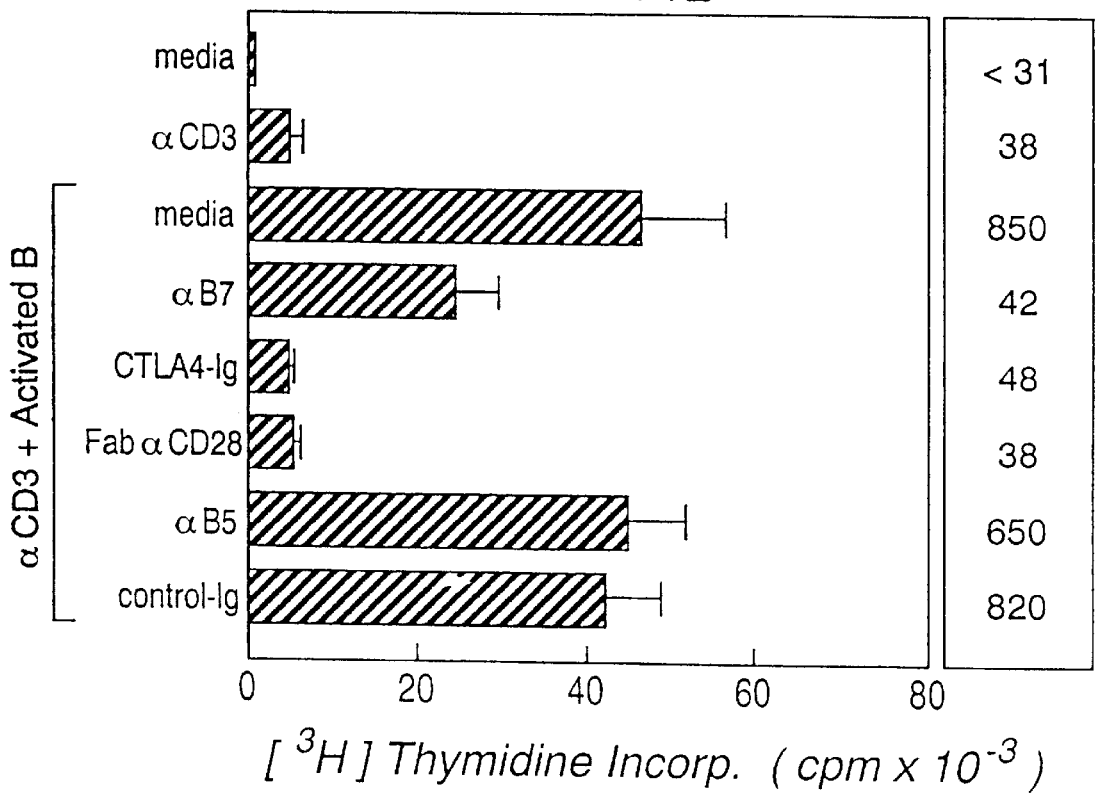

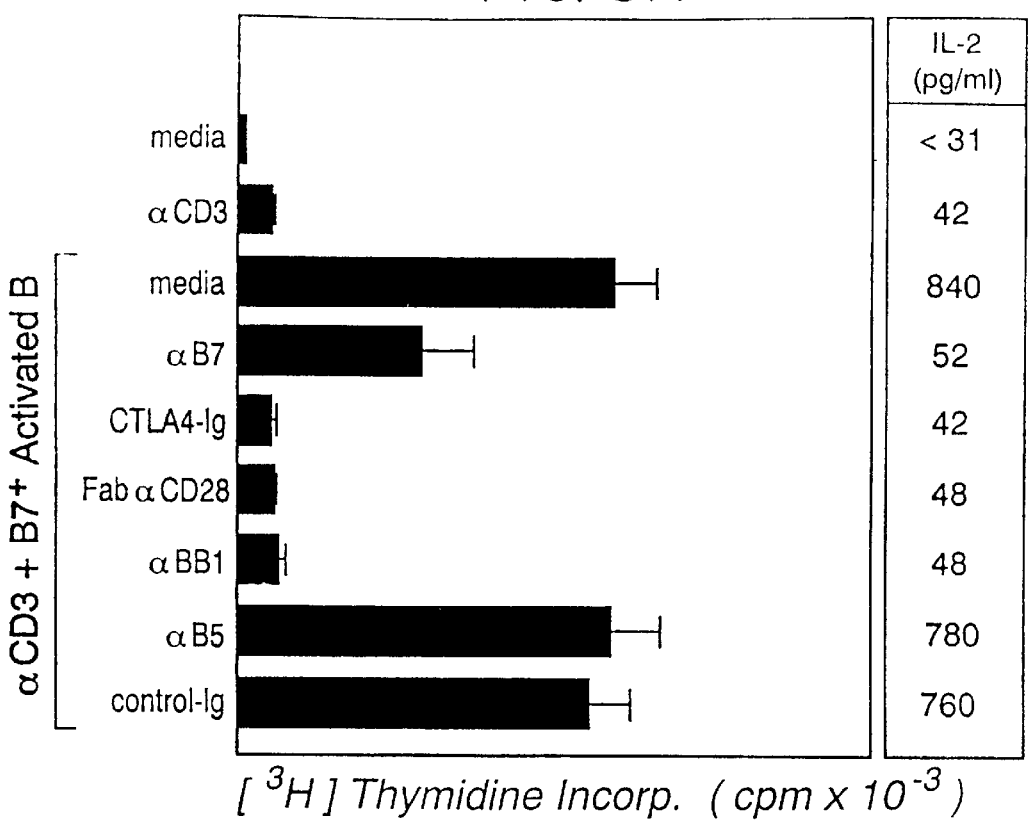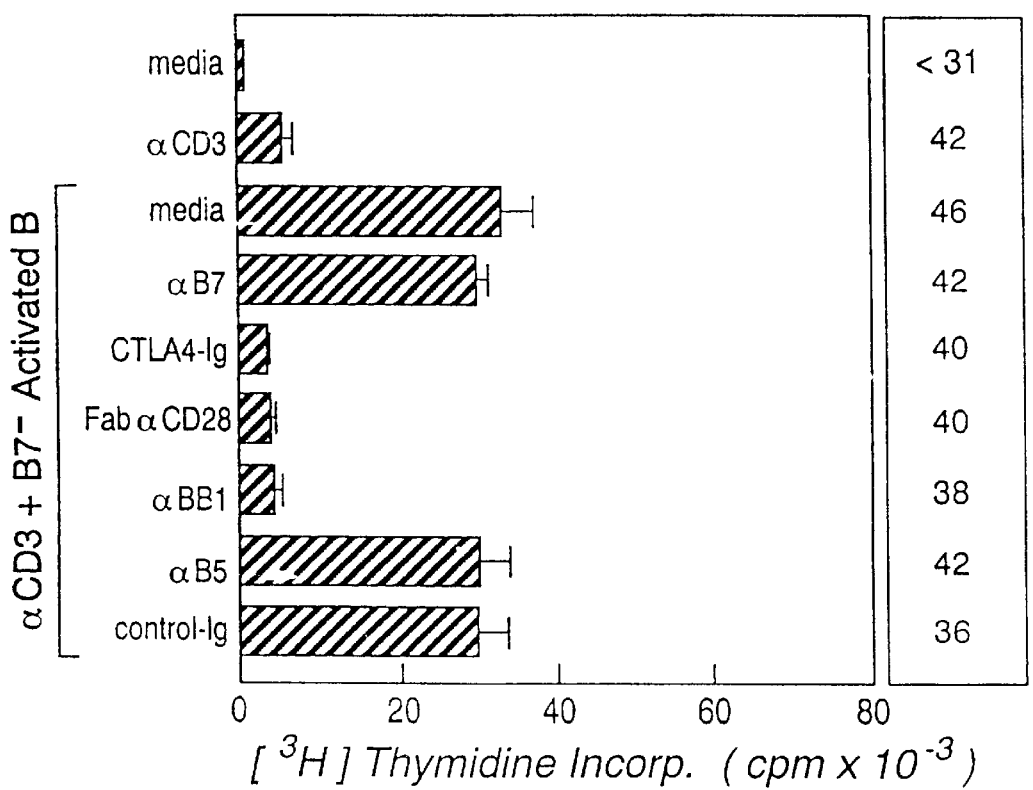

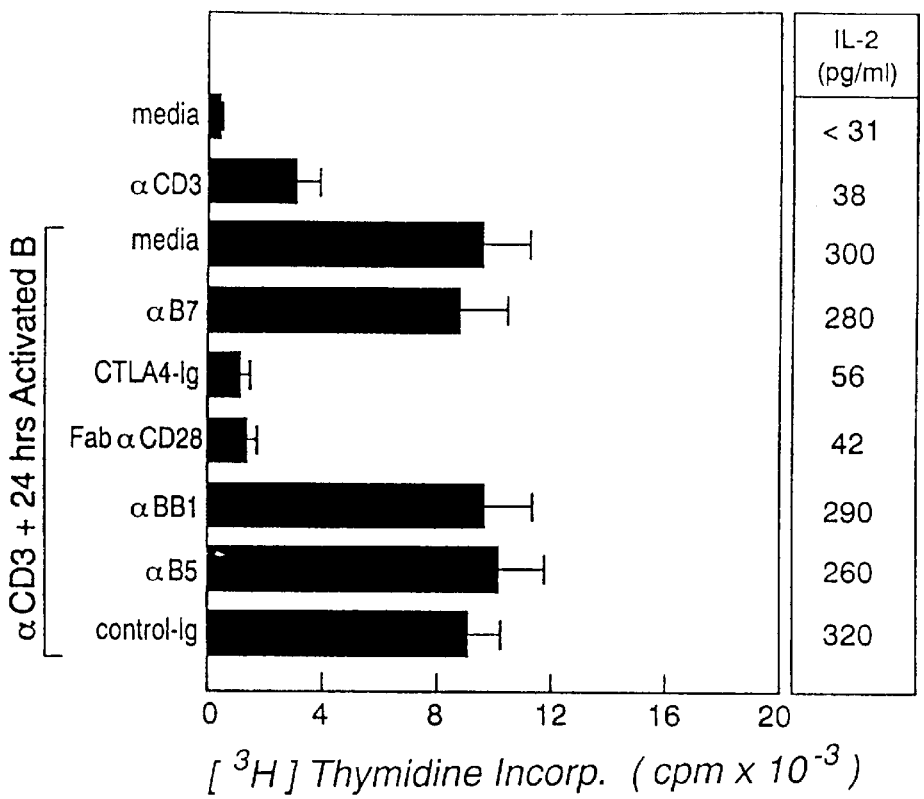
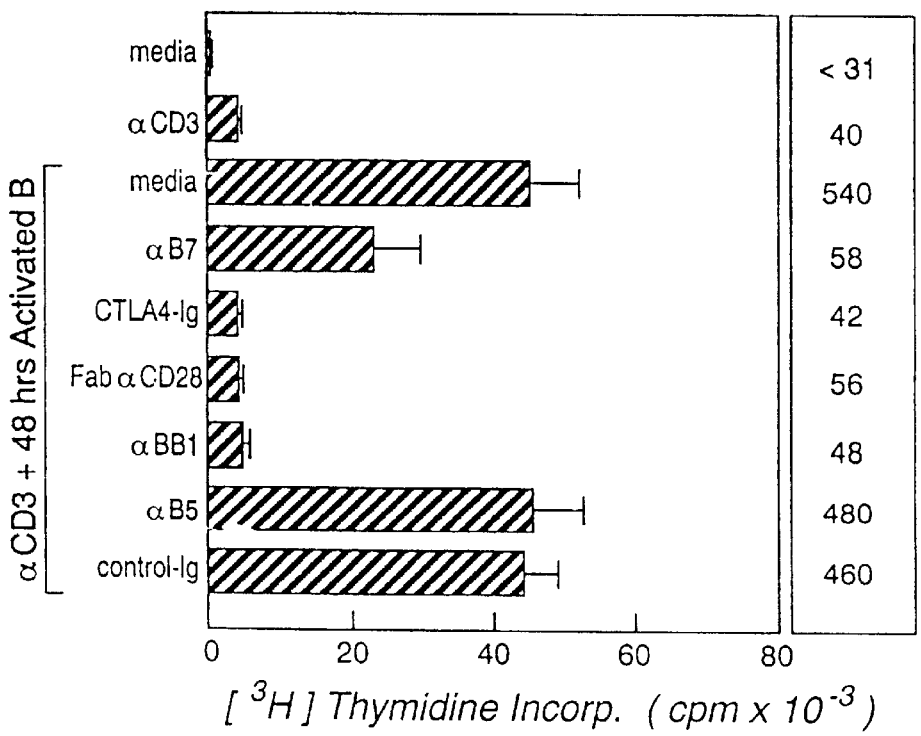

FIG. 8A

```
1    CACAGGGTGAAAGCTTTGCTTCTCTGCTGCTGTAACAGGACTAGCACACAGACACACGGATGAGTGGGGTC    70
71   ATTTCCAGATATTAGGTCACAGCAGAAGCAGCCAAAATGGATCCCCAGTGCACTATGGGACTGAGTAACA    140
12       M  D  P  Q  C  T  M  G  L  S  N                                      11
141  TTCTCTTTGTGATGGCCTTCCTGCTCCTCTCTGGTGCTGCTCCTCTGAAGATTCAAGCTTATTTCAATGAGAC   210
12   I  L  F  V  M  A  F  L  L  S  G  A  A  P  L  K  I  Q  A  Y  F  N  E  T    35
                                    ^                                  #
211  TGCAGACCTGCCATGCCAATTGCAAACTCTCAAAACCAAGCCTGAGTGAGCTAGTAGTATTTTGGCAG       280
36   A  D  L  P  C  Q  F  A  N  S  Q  N  Q  S  L  S  E  L  V  V  F  W  Q       58
                *                       #
281  GACCAGGAAAACTTGGTTCTGAATGAGGTATACTTAGGCAAAGAGAAATTTGACAGTGTTCATTCCAAGT    350
59   D  Q  E  N  L  V  L  N  E  V  Y  L  G  K  E  K  F  D  S  V  H  S  K       81
351  ATATGGGCCGCACAAGTTTTGATTCGGACAGTTGGACCCTGAGACTTCACAATCTTCAGATCAAGGACAA    420
82   Y  M  G  R  T  S  F  D  S  D  S  W  T  L  R  L  H  N  L  Q  I  K  D  K   105
```

FIG. 8B

```
421  GGGCTTGTATCAATGTATCATCCATCACAAAAGCCCACAGGAATGATTCGCATCCACCAGATGAATTCT  490
106    G  L  Y  Q  C  I  I  H  H  K  K  P  T  G  M  I  R  I  H  Q  M  N  S   128
              *

491  GAACTGTCAGTGCTGCTAACTTCAGTCAACCTGAAATAGTACCAATTTCTAATATAACAGAAAATGTGT  560
129    E  L  S  V  L  A  N  F  S  Q  P  E  I  V  P  I  S  N  I  T  E  N  V   151
                    #

561  ACATAAATTTGACCTGCTCATCTATACACGGTTACCCAGAACCTAAGAAGATGAGTGTTTTGCTAAGAAC  630
152    Y  I  N  L  T  C  S  S  I  H  G  Y  P  E  P  K  K  M  S  V  L  L  R  T  175
              *

631  CAAGAATTCAACTATCGAGTATGATGGTATTATGCAGAAATCTCAAGATAATGTCACAGAACTGTACGAC  700
176    K  N  S  T  I  E  Y  D  G  I  M  Q  K  S  Q  D  N  V  T  E  L  Y  D   198
        #

701  GTTTCCATCAGCTTGTCTGTTTCATTCCCTGATGTTACGAGCAATATGACCATCTTCTGTATTCTGGAAA  770
199    V  S  I  S  L  S  V  S  F  P  D  V  T  S  N  M  T  I  F  C  I  L  E   221
                                              #           *

771  CTGACAAGACGCGGCTTTTATCTTCCACCTTTCTCTATAGAGCTTGAGGACCCTCAGCCTCCCCCAGACCA  840
222    T  D  K  T  R  L  L  S  S  P  F  S  I  E  L  E  D  P  Q  P  P  P  D  H  245
```

FIG. 8C

```
841   CATTCCTTGGATTACAGCTGTACTTCCAACAGTTATTATATGTGTGATGGTTTCTGTCTAATTCTATGG   910
246    I  P  W  I  T  A  V  L  P  T  V  I  I  C  V  M  V  F  C  L  I  L  W    268
911   AATGGAAGAAGAAGAAGCGGCCTCGCAACTCTTATAATGTGGAACCAACACAATGGAGAGGGAAGAGA   980
269    K  W  K  K  K  K  R  P  R  N  S  Y  K  C  G  T  N  T  M  E  R  E  E    291
981   GTGAACAGACCAAGAAAAGAGAAAAATCCATATACCTGAAAGATCTGATGAAGCCCAGCGTGTTTTAA  1050
292    S  E  Q  T  K  K  R  E  K  I  H  I  P  E  R  S  D  E  A  Q  R  V  F  K  315
1051  AAGTTCGAAGACATCTTCATGGACAAAAGTGATACATGTTTTTAATTAAAGAGTAAAGCCCAAAAAAAA  1120
316    S  S  K  T  S  S  C  D  K  S  D  T  C  F  *                            329
```

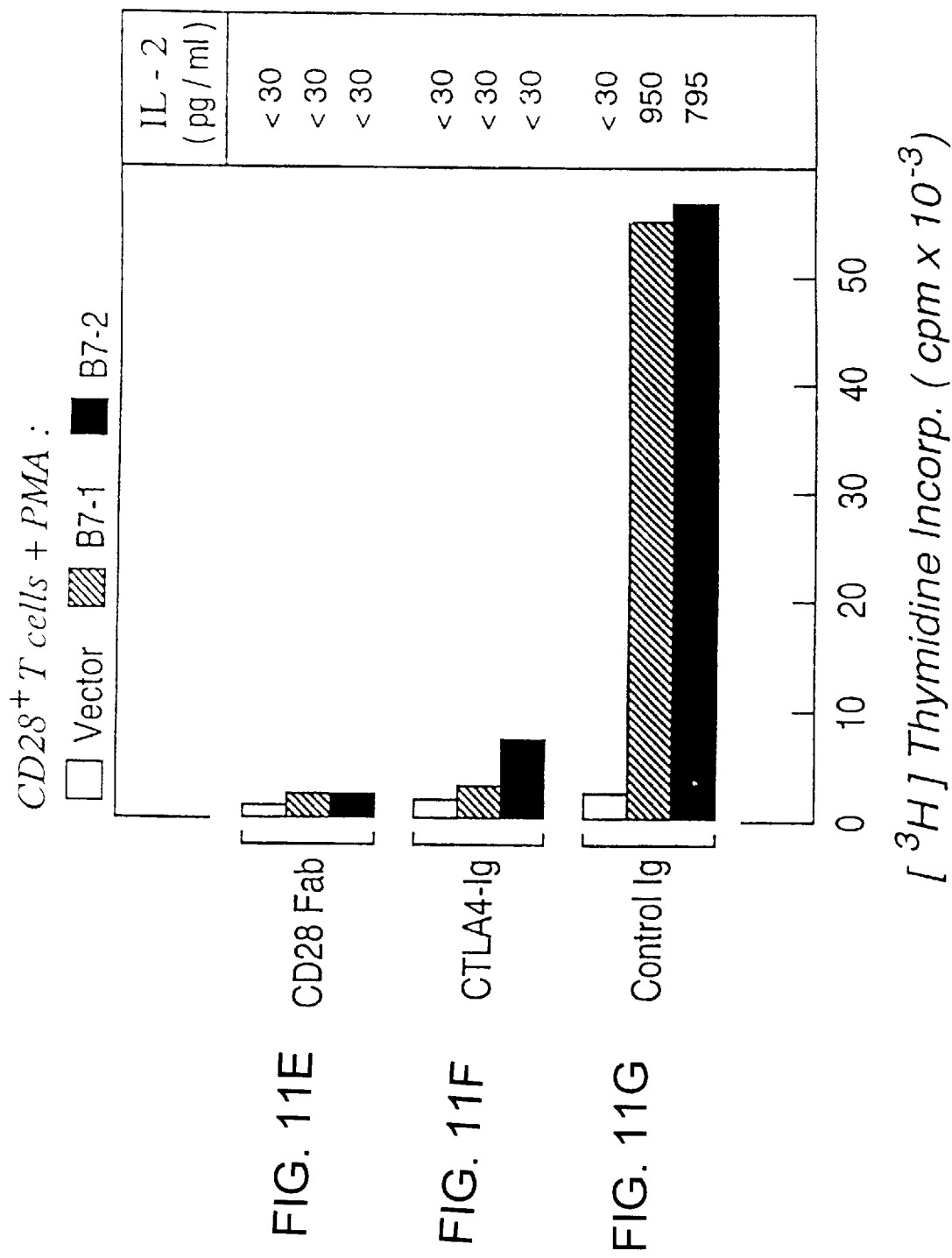

FIG. 12

T + PMA +

| | Vector | B7-1 | B7-2 | PHA |
|---|---|---|---|---|
| media | <30 | 850 | 300 | 1750 |
| 133 | <30 | <30 | 310 | 1600 |
| BB1 | <30 | <30 | 250 | 1550 |
| CTLA4Ig | <30 | <30 | <30 | 1900 |
| CIg | <30 | 850 | 270 | 1650 |
| CD28 Fab | <30 | <30 | <30 | 1500 |
| B6 | <30 | 890 | 290 | 1650 |

FIG. 13

T7(F)  5'd[TAATACGACTCACTATAGGG]3'

CDM8(R)  5'd[TAAGGTTCCTTCACAAAG]3'

CDM8 REV(2)  5'd[ACTGGTAGGTATGGAAGATCC]3'

HBX29-5P(2R)  5'd[ATGCGAATCATTCCTGTGGGC]3'

HBX29-5P(2F)  5'd[AAAGCCCACAGGAATGATTCG]3'

HBX29-5P  5'd[CTCTCAAAACCAAABCCTGAG]3'

5PA  5'd[TTAGGTCACAGCAGAAGCAGC]3'

5P(3FA)  5'd[TCTGGAAACTGACAAGACGCG]3'

HBX-295P(1R)  5'd[CTCAGGCTTTGGTTTTGAGAG]3'

HBX29-3P(1R)  5'd[CACTCTCTTCCCTCTCCATTG]3'

HBX29-5P(3R)  5'd[GACAAGCTGATGGAAACGTCG]3'

HBX29-3P(1F)  5'd[CAATGGAGAGGGAAGAGAGTG]3'

FIG. 14A

```
hB7-1    1 M..GHTRRQGTSPSKCPYLNFFQLLV.LAGLSHFCSGV.IHVTKEVKEVA   46
           -  ----------             --- -- --- -
hB7-2    1 M......DPQCTMGLSN......ILFVMAFLLSGA...APLKIQAYFNETA   36
                                       ---       -   -
mB7      1 MACNCQLMQDTPLLKFPCPRLILFVLLIRLSQVSSDVDEQLSKSVKDKV    50
                                           .

hB7-1   47 TLSCGHNVSVEE.LAQTRIYWQKEKKMVLT.MMSGDMNI...WPEYKNRT   91
            - ---- ---              --                --- -
hB7-2   37 DLPCQFANSQNQSLSELVVFWQDQENLVLNEVYLGKEKFDSVHSKYMGRT   86
            - -      ---                 --                -
mB7     51 LLPCRY.NSPHEDESEDRIYWQKHDKVVLS.VIAGKLKV...WPEYKNRT   95
                                           .

hB7-1   92 IFDITNNLSIVILALRPSDEGTYECVVLKYEKDAFKREHLAEVTLSVKAD  141
             -  -- -  --- --   -----  ---  ---  -     ---- -
hB7-2   87 SFD.SDSWTLRLHNLQIKDKGLYQCIIHHKKPTGMIRIHQMNSELSVLAN  135
             -                    ---           -      --- -
mB7     96 LYDNTT.YSLIILGLVLSDRGTYSCVVQKKERGTYEVKHLALVKLSIKAD  144
                                           .

hB7-1  142 FPTPSISDFEIPTSNI.RRIICSTSGGFPEPH....LSWLENGEELNAIN  186
             --                          ---        ------
hB7-2  136 FSQPEIVPISNITENVYINLTCSSIHGYPEPKKMSVLLRTKNSTIEYDGI  185
             --                          ---        ------
mB7    145 FSTPNITESGNPSADT.KRITCFASGGFPKPR....FSWLENGRELPGIN  189
                                           .
```

FIG. 14B

```
hB7-1  187  TTVSQDPETELYAVSSKLDFN...MTTNHSFMCLIKYGHLRVNQTFNWNT  233
             |||  ||||| ||  |||   |||||| || ||||
hB7-2  186  MQKSQDNVTELYDVSISLSVSFPDVTSNMTIFCILETDKTRLLSSPFSIE      235
             |||  |||||| || |||
mB7    190  TTISQDPESELYTISSQLDFN...TTRNHTIKCLIKYGDAHVSEDFTWEK      236 hB7-1  234  TKQEHF.PDNLLPSWAITLISVNGIFVICCLTYCFAPRCRERRRNERLRR       282
                       ||  ||  || |||  |   ||
hB7-2  236  .LEDPQPPPDHIPWITAVLP....TVIICVMVFCLLWKKKKRPRNSY         280
                       ||   |  |
mB7    237  PPEDPPPDSKNTLVLFGAGFGAVITVVVIVVIIKCFCKHRSCFRRNEA.SR     285 hB7-1  283  ESVRPV*                                                 288
hB7-2  281  KCG...TNTMEREESEQTKKREKIHIPERSDEAQRVFKSSKTSSCDKSDT      327
mB7    286  ETNNSLTFGPEEALAEQTVFL*                                  306 hB7-2  328  CG*                                                     329
```

B7-2: A CTLA4/CD28 LIGAND

GOVERNMENT FUNDING

This invention was made with government support under CA-40216-08 awarded by the National Institutes of Health. The U.S. government therefore has certain rights in this invention.

BACKGROUND OF THE INVENTION

To induce antigen-specific T cell activation and clonal expansion, two signals provided by antigen-presenting cells (APCs) must be delivered to the surface of resting T lymphocytes (Jenkins, M. and Schwartz, R. (1987) *J. Exp. Med* 165, 302–319; Mueller, D. L., et al. (1990) *J. Immunol.* 144, 3701–3709; Williams, I. R. and Unanue, E. R. (1990) *J. Immunol.* 145, 85–93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) *Science* 248, 1349–1356). Costimulation is neither antigen-specific, nor MHC restricted and is thought to be provided by one or more distinct cells surface molecules expressed by APCs (Jenkins, M. K., et al. (1988) *J. Immunol.* 140, 3324–3330; Linsley, P.S., et al. (1991) *J. Exp. Med* 173, 721–730; Gimmi, C. D., et al., (1991) *Proc. Natl. Acad Sci. USA.* 88, 6575–6579; Young, J. W., et al. (1992) *J. Clin. Invest.* 90, 229–237; Koulova, L., et al. (1991) *J Exp. Med* 173, 759–762; Reiser, H., et al. (1992) *Proc. Natl. Acad. Sci. USA.* 89, 271–275; van-Seventer, G. A., et al. (1990) *J. Immunol.* 144, 4579–4586; LaSalle, J. M., et al., (1991) *J. Immunol.* 147, 774–80; Dustin, M. I., et al., (1989) *J. Exp. Med.* 169, 503; Armitage, R. J., et al. (1992) *Nature* 357, 80–82; Liu, Y., et al. (1992) *J. Fxp. Med.* 175, 437–445).

Considerable evidence suggests that the B7 protein, expressed on APCs, is one such critical costimulatory molecule (Linsley, P. S., et al., (1991) *J. Exp. Med* 173, 721–730; Gimmi, C. D., et al., (1991) *Proc. Natl. Acad Sci. USA.* 88, 6575–6579; Koulova, L., et al., (1991) *J. Exp. Med.* 173, 759–762; Reiser, H., et al. (1992) *Proc. Natl. Acad. Sci. USA.* 89, 271–275; Linsley, P. S. et al. (1990) *Proc. Natl. Acad. Sci. USA.* 87, 5031–5035; Freeman, G. J. et al. (1991) *J. Exp. Med* 174,625–631.). B7 is the counter-receptor for two ligands expressed on T lymphocytes. The first ligand, termed CD28, is constitutively expressed on resting T cells and increases after activation. After signaling through the T cell receptor, ligation of CD28 induces T cells to proliferate and secrete IL-2 (Linsley, P. S., et al. (1991) *J. Exp. Med.* 173, 721–730; Gimmi, C. D., et al. (1991) *Proc. Natl. Acad. Sci. USA.* 88, 6575–6579; Thompson, C. B., et al. (1989) Proc. Natl. Acad. Sci. USA. 86, 1333–1337; June, C. H., et al. (1990) *Immunol. Today.* 11, 211–6; Harding, F. A., et al. (1992) *Nature.* 356, 607–609.). The second ligand, termed CTLA4 is highly homologous to CD28 but is not expressed on resting T cells and appears following T cell activation (Brunet, J. F., et al., (1987) *Nature* 328, 267–270). Although B7 has a higher affinity for CTLA4 than for CD28 (Linsley, P. S., et al., (1991) *J. Exp. Med.* 174, 561–569), its function is still unknown. The importance of the B7:CD28/CTLA4 costimulatory pathway has been demonstrated in vitro and in several in vivo model systems. Blockade of this costimulatory pathway results in the development of antigen specific tolerance in murine and humans systems (Harding, F. A., et al. (1992) *Nature.* 356, 607–609; Lenschow, D. J., et al. (1992) *Science.* 257, 789–792; Turka, L. A., et al. (1992) *Proc. Natl. Acad. Sci. USA.* 89, 11102–11105; Gimmi, C. D., et al. (1993) *Proc. Natl. Acad. Sci USA* (90 6586–6590); Boussiotis, V., et al *J. Exp. Med.* (accepted for publication)). Conversely, expression of B7 by B7 negative murine tumor cells induces T-cell mediated specific immunity accompanied by tumor rejection and long lasting protection to tumor challenge (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690.). Therefore, manipulation of the B7:CD28/CTLA4 pathway offers great potential to stimulate or suppress immune responses in humans.

SUMMARY OF THE INVENTION

This invention pertains to isolated nucleic acids encoding novel CTLA4/CD28 ligands which costimulate T cell activation. CTLA4/CD28 ligands within the scope of the invention include counter-receptors on the surface of B lymphocytes capable of binding either CTLA4, CD28 or both CTLA4 and CD28. Such CTLA4/CD28 binding counter-receptors are refered to herein as B lymphocyte antigens, capable of providing costimulation to activated T cells to thereby induce T cell proliferation and/or lymphokine secretion. Preferred B lymphocyte antigens include B7-2 and B7-3 and soluble fragments or derivatives thereof which bind CTLA4 and/or CD28. In one embodiment, an isolated nucleic acid which encodes the human B7-2 B lymphocyte antigen is provided. Preferably, the nucleic acid is a DNA molecule comprising at least a portion of a nucleotide sequence encoding B7-2, shown in FIG. 8, SEQ ID NO:1 or a DNA molecule capable of hybridizing to a nucleotide sequence shown in FIG. 8, SEQ ID NO:1 under appropriate conditions (e.g., moderate stringency conditions for the hybridization of 2.0×SSC at 50° C.), or a DNA molecule which differs from the nucleotide sequence shown in FIG. 8, SEQ ID NO:1 due to degeneracy in the genetic code. The invention further pertains to a DNA molecule comprising a nucleotide sequence encoding the B7-2 antigen whose amino acid sequence is shown in FIG. 8, SEQ ID NO:2. Nucleic acids which encode proteins that are at least about 30% similar to the amino acid sequence set forth in SEQ ID NO:2 are also within the scope of the invention.

The nucleic acids obtained in accordance with the present invention can be inserted into various expression vectors, which in turn direct the synthesis of the corresponding proteins or peptides in a variety of hosts, particularly eucaryotic cells, such as mammalian and insect cell culture and procaryotic cells such as *E. coli*. Expression vectors within the scope of the invention comprise a nucleic acid sequence encoding at least one novel B lymphocyte antigen as described herein, and a promoter operatively linked to the nucleic acid sequence. In one embodiment, the expression vector comprises a DNA sequence encoding the B7-2 antigen and a DNA sequence encoding another B lymphocyte antigen, such as the previously characterized B7 activation antigen, referred to herein as B7-1 . Such expression vectors can be used to transfect host cells to thereby produce proteins or peptides, including fusion proteins or peptides encoded by nucleic acid sequences as described herein.

The present invention further pertains to isolated B lymphocyte antigens, including the B7-2 and B7-3 protein antigens. A preferred B lymphocyte antigen is B7-2 , comprising an amino acid sequence shown in FIG. 8, SEQ ID NO:2, or portion thereof. B lymphocyte activation antigens comprise at least a portion of the mature form of the B7-2 or B7-3 antigen and preferably comprise a soluble form of the protein.

Nucleic acid probes useful for assaying a biological sample for the presence of B cells expressing the B lymphocyte antigens B7-2 and B7-3 are also within the scope of the invention. In addition, isolated B lymphocyte antigens and fusion proteins or hybrid fusion protein constructs comprising at least a portion of a B lymphocyte antigen (e.g., B7-1 , B7-2 , B7-3) are provided. For example, a fusion protein comprising an extracellular domain portion of a B lymphocyte antigen fused to another protein, such as human immunoglobulin C gamma 1 (Cγ1), that alters the solubility, binding affinity and/or valency of a B lymphocyte antigen are disclosed. In one embodiment, a DNA molecule encoding an extracellular domain portion of the B7-2 protein can be joined to DNA encoding amino acid residues of a sequence corresponding to the hinge CH2 and CH3 regions of human Ig Cγ1 to form a DNA fusion product which encodes a B7-2 Ig fusion protin. In another embodiment, a hybrid fusion protein is produced comprising a fragment of the extracellular domain of the B7-1 antigen and a fragment of the extracellular domain of B7-2 coupled to the hinge CH2 and CH3 of human Ig Cγ1 (see e.g., Linsley et al. (1991) *J. Exp. Med.* 173:721–730). Such fusion proteins can be used to enhance or suppress T cell-mediated immune responses in vivo. Isolated proteins and polypeptides of the invention can be administered to a subject to either upregulate or block the expression of one or more B lymphocyte antigens or the ligation of one or more B lymphocyte antigens to their natural ligand on T cells to thereby provide enhancement or suppression of T cell-mediated immune responses.

Another embodiment of the invention provides antibodies, preferably monoclonal antibodies, specifically reactive with a novel B lymphocyte antigen as described herein.

A still further aspect of the invention involves the use of the nucleic acids of the invention, especially the cDNAs, to enhance the immunogenicity of a mammalian cell. In preferred embodiments, the mammalian cell is a tumor cell, such as a sarcoma, a lymphoma, a melanoma, a neuroblastoma, a leukoma and a carcinoma, or an antigen presenting cell, such as a macrophage, which is transfected to allow expression of the novel B lymphocyte antigens of the invention. Macrophages that express B lymphocyte antigens, such as the B7-2 antigen can be used as antigen presenting cells, which, when pulsed with an appropriate pathogen-related antigen or tumor antigen, enhance T cell activation and immune stimulation.

Mammalian cells can be transfected with a suitable expression vector comprising a gene encoding a B lymphocyte antigen, such as the B7-2 antigen ex vivo and then introduced into the host mammal, or alternatively, they can be transfected with the gene in vivo via gene therapy techniques. For example, the B7-2 or B7-3 gene can be transfected alone, or in combination with genes encoding other costimulatory molecules. In enhancing the immunogenicity of tumors which do not express Class II MHC molecules, it may be beneficial to express the appropriate class II molecules in the mammalian cells to be transfected with a gene encoding a B lymphocyte antigen, as described herein.

The invention also provides methods for inducing tolerance in a subject by, for example, blocking the functional interaction of the novel B lymphocyte antigens of the invention, e.g., B7-2 and B7-3 , to their natural ligand(s) on T cells or other immune system cells, to thereby block co-stimulation through the receptor-ligand pair. In one embodiment, molecules that can be used to block the interaction of the human B7-2 antigen to its natural ligands (e.g., CTLA4 and CD28) include soluble B7-2 , antibodies that block the binding of B7-2 to its ligands and fail to deliver a co-stimulatory signal (so called "blocking antibodies") and B7-2 -Ig fusion proteins, which can be produced in accordance with the teaching of the present invention. Inducing tolerance in a subject in accordance with the methods described herein may be useful prophylactically, in preventing immune disorders such as trasplantation rejection (solid organ and bone marrow) and graft versus host disease, especially in autologous bone marrow transplantation. The methods of the invention may also be useful therapeutically, in the treatment of autoimmune diseases, transplantation rejection, and established graft versus host disease in a subject.

BRIEF DESCRIPTION OF THE DRAWINGS

FIGS. 1A and 1B are a graphic representation of the response of CD4+T cells to costimulation provided by either B7 (B7-1) transfected CHO cells (panel a) or syngeneic activated B lymphocytes (panel b) cultured in media, anti-CD3 alone, or anti-CD3 in the presence of the following monoclonal antibodies or recombinant proteins: αB7 (B7-1); CTLA4-Ig; Fab αCD28; or control Ig fusion protein (isotype control for CTLA4Ig); or αB5 (the isotype control for anti-B7). $^3$H-Thymidine incorporation was assessed for the last 15 hours of a 72 hours culture. IL-2 was assessed by ELISA in supernatants of 24 hours of culture (Detection limits of the assay: 31–2000 pg/ml). The figure is representative of seventeen experiments.

FIGS. 3A and 3B are a graphic representations of the response of CD4+T cell costimulation provided by B7-1 positive (panel a) or B7-1 negative (panel b) activated syngeneic B lymphocytes cultured in media, anti-CD3 alone, or anti-CD3 in the presence of the following monoclonal antibodies or recombinant proteins: αBB-1 (B7-1 and B7-3); αB7 (B7-1); CTLA4-Ig; Fab αCD28; control Ig fusion protein or αB5. $^3$H-Thymidine incorporation was assessed for the last 15 hours of a 72 hours culture. IL-2 was assessed in supernatants of 24 hours of culture by ELISA (Detection limits of the assay: 31–2000 pg/ml). The results are representative of ten experiments.

FIGS. 7A and 7B are graphic representations of the response of CD4+T cells to costimulation provided by syngeneic B lymphocytes activated by sIg crosslinking for 24 hours (panel a) or 48 hours (panel b) and cultured in media, anti-CD3 alone, or anti-CD3 in the presence of the following monoclonal antibodies or recombinant protein: αB7(B7-1 ); (CTLA4-Ig; Fab αCD28; and αB5. $^3$H-Thymidine incorporation was assessed for the last 15 hours of a 72 hours culture. IL-2 was assessed by ELISA in supernatants of 24 hours of culture (Detection limits of the assay: 31–2000 pg/ml). The results are representative of five experiments.

FIGS. 8A–8C show the nucleotide (SEQ ID No:1) and deduced amino acid sequence (SEQ ID No:2) of the B lymphocyte activation antigen B7-2 (hBx-clone29).

FIG. 12 is a graphic representation of the amount of interleukin-2 (IL-2) produced by CD28+T cells submitogenically stimulated with PMA and then treated with COS cells transfected with vector alone (vector), or with vectors expressing B7-2 (B7-1 ) or B7-2 (B7-2). Cells were also treated with phytohemaglutinin (PHA) to produce maximal IL-2. Inhibition of proliferation was determined by adding mAbs 133, BB-1, B5, or CD28 Fab, or by adding recombinant protein CTLA4Ig or control Ig (CIg). COS cells expressing B7-1 produce approximately twice the amount of IL-2 as do COS cells expressing B7-2. This IL-2 production is inhibited by mAbs 133, BB-1, CD28 Fab for COS cells expressing B7-1 but only by CTLA4Ig for COS cells expressing B7-2.

FIG. 13 shows primers [T7(F) (SEQ ID NO:3), CDM8 (R)(SEQ ID NO:4), CDM8REV(2) (SEQ ID NO:5), HBX29-5P(2R) (SEQ ID NO:6), HBX29-5P(2F) (SEQ ID NO:7), HBX29-5P (SEQ ID NO:8), 5PA (SEQ ID NO:9), 5P(3FA) (SEQ ID NO:10), HBX29-5P(1R) (SEQ ID NO:11), HBX29-3P(1R) (SEQ ID NO:12), HBX29-5P(3R) (SEQ ID NO:13), HBX29-3P(1P) (SEQ ID NO:14)] used in the cloning and sequencing of the B7-2 protein.

FIG. 14 shows the amino acid sequence homology between the human B7-1 protein (h B7-1)(SEQ ID NO:22 and 23), the human B7-2 protein (h B7-2) (SEQ ID NO:2) and the murine B7 protein (m B7)(SEQ ID NO:24 and 25).

DETAILED DESCRIPTION OF THE INVENTION

Figure 2A:
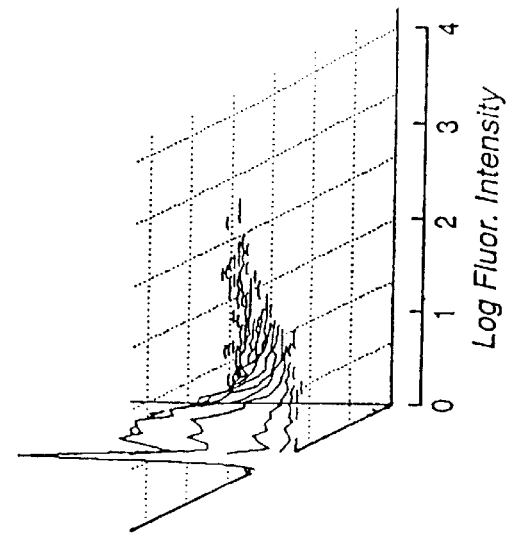
FIGS. 2A–C are graphs of log fluorescence intensity of cell surface expression of B7 on splenic B cells activated with surface immunoglobulin (sIg) crosslinking. After 72 hours of activation, the B cells were separated into B7-1 positive and negative populations by staining with anti-B7-1 (B 1.1) monoclonal antibody and fluorescin isothiocyanate (FITC) labeled goat antimouse immunoglobulin and separation on a fluorescent activated cell sorter (FACS). The total (panel a), B7-1 positive (panel b) and B7 negative (panel c) activated B cells were stained with anti-B7 monoclonal antibody (133) and FITC labeled goat anti-mouse immunoglobulin and analyzed by flow cytometry.

In addition to the previously characterized B lymphocyte activation antigen, B7 (referred to herein as B7-1) activated human B lymphocytes express other novel CTLA4/CD28 binding counter-receptors. These T cell costimulatory molecules, referred to herein as B lymphocyte activation antigens B7-2 and B7-3, have been discovered and characterized. The B lymphocyte activation antigen B7- 2 is expressed by B cells al about 24 hours following stimulation with either anti-immunoglobulin or anti-MHC class II monoclonal antibody. The B7-2 antigen induces detectable IL-2 secretion and T cell proliferation. At about 48 to 72 hours post activation, B cells express both B7-1 and a third CTLA4 counter-receptor identified by a monoclonal antibody BB-1 (Yokochi, T., et al. (1982) *J. Immunol.* 128, 823–827), termed B7-3. The B7-3 antigen is also expressed on B7 negative activated B cells and can costimulate T cell proliferation without detectable IL-2 production, indicating that the B7-1 and B7-3 molecules are distinct. B7-3 is expressed on a wide variety of cells including activated B cells, activated monocytes, dendritic cells, Langerhans cells and keratinocytes. At 72 hours post B cell activation, the expression of B7-1 and B7-3 begins to decline. The presence of these CTLA4/CD28 binding counter-receptors on the surface of activated B lymphocytes indicates that T cell costimulation is regulated, in part, by the temporal expression of these molecules following B cell activation.

Accordingly, one aspect of this invention pertains to isolated nucleic acids having a nucleotide sequence encoding novel B lymphocyte activation antigens, fragments thereof or equivalents thereof. The term nucleic acid as used herein is intended to include such fragments or equivalents. Preferably, the nucleic acid is a cDNA molecule encoding at least a portion of the B7-2 activation antigen. A nucleic acid sequence encoding a novel B lymphocyte antigen, such as the B7-2 antigen, may be obtained from mRNA present in activated B lymphocytes. It should also be possible to obtain nucleic acid sequences encoding B lymphocyte antigens from B cell genomic DNA. For example, the gene coding for the B7-2 activation antigen can be cloned from either a cDNA or a genomic library in accordance with protocols herein described. A cDNA nucleotide sequence for the B7-2 activation antigen can be obtained by isolating total mRNA from an appropriate cell line. Double stranded cDNAs are then prepared from the total mRNA. Subsequently, the cDNAs can be inserted into a suitable plasmid or bacteriophage vector using any one of a number of known techniques. Genes encoding novel B lymphocyte antigens can also be cloned using established polymerase chain reaction techniques in accordance with the nucleic acid sequence information provided by the invention. The nucleic acid sequences of the invention can be DNA or RNA. A preferred nucleic acid is a cDNA encoding the human B7-2 antigen having the sequence depicted in FIG. 8 (SEQ ID NO:1) or equivalents thereof.

The term equivalent is intended to include nucleotide sequences encoding functionally equivalent B lymphocyte antigens. For example, DNA sequence polymorphisms within the nucleotide sequence of a B lymphocyte activation antigen, such as B7-2 (especially those within the third base of a codon) may result in "silent" mutations which do not affect the amino acid sequence of the B7-2 protein. However, it is expected that DNA sequence polymorphisms that do lead to changes in the amino acid sequence of the B7-2 antigen will exist within a population. It will be appreciated by one skilled in the art that these variations in one or more nucleotides (up to about 3–4% of the nucleotides) of the nucleic acid sequences encoding novel B lymphocyte antigens may exist among individuals within a population due to natural allelic variation. Any and all such nucleotide variations and resulting amino acid polymorphisms are within the scope of the invention. Furthermore, there may be one or more isoforms or related, cross-reacting family members of the novel B lymphocyte antigens described herein. Such isoforms or family members are defined as proteins related in function and amino acid sequence to a B lymphocyte antigen (e.g., the B7-2 antigen), but encoded by genes at different loci.

A fragment of the nucleic acid sequence encoding a novel B lymphocyte antigen is defined as a nucleotide sequence having fewer nucleotides than the nucleotide sequence encoding the entire amino acid sequence of the B lymphocyte antigen. Nucleic acid fragments which encode polypeptides which retain the ability to bind to their natural ligand(s) on T cells and either amplify or block activated T cell mediated immune responses (as evidenced by, for example, lymphokine production and/or T cell proliferation by T cells that have received a primary activation signal) are considered within the scope of the invention. For example, nucleic acid fragments which encode polypeptides of a B lymphocyte antigen which retain the ability of the antigen to bind CTLA4 and/or CD28 and deliver a costimulatory signal to T lymphocytes are within the scope of the invention. In addition, nucleic acid fragments within the scope of the invention include those capable of hybridizing with nucleic acid from other animal species for use in screening protocols to detect novel proteins that are cross-reactive with those B lymphocyte activation antigens described herein. These and other fragments are described in detail herein. Generally, the nucleic acid sequence encoding a fragment of a B lymphocyte antigen will be selected from the bases coding for the mature protein, however, in some instances it may be desirable to select all or part of a fragment or fragments from the leader sequence portion of a nucleic acid sequence. Nucleic acid sequences within the scope of the invention may also contain linker sequences, modified restriction endonuclease sites and other sequences useful for molecular cloning, expression or purification of recombinant protein or fragments thereof. These and other modifications of nucleic acid sequences are described in detail herein.

This invention further pertains to expression vectors containing a nucleic acid sequence encoding at least one novel B lymphocyte antigen, as described herein, operably linked to at least one regulatory sequence. Operably linked is intended to mean that the nucleotide acid sequence is linked to a regulatory sequence in a manner which allows expression of the nucleotide sequence. Regulatory sequences are art-recognized and are selected to direct expression of the desired protein in an appropriate host cell. Accordingly, the term regulatory sequence includes promoters, enhancers and other expression control elements. Such regulatory sequences are described in Goeddel, *Gene Expression Technology. Methods in Enzymology* 185, Academic Press, San Diego, Calif. (1990)). It should be understood that the design of the expression vector may depend on such factors as the choice of the host cell to be transfected and/or the type of protein desired to be expressed. In one embodiment, the expression vector comprises a nucleic acid encoding at least a portion of the B7-2 protein. In another embodiment, the expression vector comprises a DNA sequence encoding the B7-2 antigen and a DNA sequence encoding another B lymphocyte antigen, such as B7-1. Such expression vectors can be used to transfect host cells to thereby produce proteins or peptides, including fusion proteins or peptides encoded by nucleic acid sequences as described herein.

Accordingly, this invention further pertains to methods of producing novel B lymphocyte antigens and portions thereof. For example, a host cell transfected with a nucleic acid vector directing expression of a nucleotide sequence coding for at least a portion of the B7-2 protein can be cultured under appropriate conditions to allow expression of B7-2 protein or peptide to occur. In addition, one or more expression vectors comprising DNA encoding at least a portion of the B7-2 protein and DNA encoding at least a portion of a second B lymphocyte antigen (e.g., B7-1, B7-3) can be used to transfect a host cell to produce fusion proteins or peptides. A recombinant expression vector comprising DNA encoding a portion of the extracellular domain of the B7-2 antigen and DNA encoding another protein, such as human immunoglobulin Cγ1, that alters the solubility, binding affinity and/or valency of the B7-2 antigen can also be produced. For example, the DNA encoding the extracellular domain of B7-2 can be joined to DNA encoding the hinge, CH2 and CH3 regions of human IgCγ1 to produce a DNA fusion construct which encodes a B7-2 Ig fusion protein. The resulting proteins or peptides may be secreted and isolated from a mixture of cells and medium containing B7-2 or other protein. Alternatively, the protein may be retained cytoplasmically and the cells harvested, lysed and the protein isolated. A culture typically includes host cells, media and other byproducts. Suitable mediums for cell culture are well known in the art. B7-2 protein can be isolated from cell culture medium, host cells, or both using techniques known in the art for purifying proteins and peptides. Techniques for transfecting host cells and purifying proteins and peptides are described in detail herein.

Transfected host cells which express novel B lymphocyte antigens (e.g., B7-2, B7-3) or portions thereof on the surface of the cell are within the scope of this invention. For example, a tumor cell such as a sarcoma, melanoma, leukemia, lymphoma, carcinoma or neuroblastoma can be transfected with an expression vector directing the expression of at least one B lymphocyte antigen on the surface of the tumor cell. Such transfected tumor cells can be used to treat tumor immunity as described in detail herein.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Another aspect of the invention pertains to isolated B lymphocyte activation antigen. The terms "isolated B lymphocyte antigen" or "isolated B7-2 protein" is intended to include functional equivalents thereof and fragments thereof. The term functional equivalent is intended to include proteins which differ in amino acid sequence from a B lymphocyte antigen, such as the B7-2 sequence depicted in FIG. 8 (SEQ ID NO:2), but where such differences result in a modified protein which functions in the same or similar manner as the B lymphocyte activation antigen or which has the same or similar characteristics of the B lymphocyte antigen. For example, a functional equivalent of B7-2 may have a modification such as a substitution, addition or deletion of an amino acid residue which is not directly involved in the function of B7-2 (i.e., the ability of B7-2 to costimulate T cell proliferation). In addition, non-naturally occurring analogues of B7-2 capable of binding CTLA4 and/or CD28 and a greater degree of homology with B7-2 than other CTLA4/CD28 binding counter receptors are considered functional equivalents. Various modifications of the B7-2 protein to produce functional equivalents of B7-2 are described in detail herein.

The term "isolated" as used throughout this application refers to a novel B lymphocyte antigen, such as the B7-2 protein, substantially free of cellular material or culture medium when produced by recombinant DNA techniques, or chemical precursors or other chemicals when chemically synthesized. Accordingly, an isolated B lymphocyte antigen or an isolated B7-2 protein is produced recombinantly or synthetically and is substantially free of cellular material and culture medium or substantially free of chemical precursors or other chemicals.

These and other aspects of this invention are described in detail in the following subsections.

Isolation of Nucleic Acid From Cell Lines

Suitable cells for use in isolating nucleic acid encoding novel B lymphocyte activation antigens include cells capable of producing mRNA coding for B lymphocyte antigens (e.g., B7-1, B7-2, B7-3) and appropriately translating the mRNA into the corresponding protein. One source of mRNA is normal human splenic B cells activated with anti-immunoglobulin or anti-MHC class II immunoglobulin or from subsets of neoplastic B cells. Expression of the B7-2 antigen in normal B cells is detectable after stimulation, with mRNA levels peaking at from about 4–12 hours after stimulation and declining slowly thereafter. Total cellular RNA can be obtained during these intervals and utilized in the construction of the cDNA library.

In addition, various subsets of neoplastic B cells are known to express B7-1 and, thus, may express B7-2 and B7-3 and can alternatively serve as a source of the mRNA for construction of the cDNA library. For example, tumor cells isolated from patients with non-Hodgkins lymphoma express B7-1 mRNA. B cells from nodular, poorly differentiated lymphoma (NPDL), diffuse large cell lymphoma (LCL) and Burkitt's lymphoma cell lines are also suitable sources of human B7-1 mRNA and, potentially B7-2 and B7-3mRNA. Myelomas generally express B7-2, but not B7-2 mRNA, and, thus can provide a source of B7-2 mRNA. The Burkitt's lymphoma cell line Raji is a particularly preferred source of B lymphocyte activation antigen mRNA.

Isolation of mRNA and Construction of cDNA Library

Total cellular mRNA can be isolated by a variety of techniques, e.g., by using the guanidinium-thiocyanate extraction procedure of Chirgwin et al., *Biochemistry*, 18: 5294–5299 (1979). According to this method, Poly (A+) mRNA is prepared and purified for use in cDNA library construction using oligo (dT) cellulose selection. cDNA is then synthesized from the poly(A+) RNA using oligo(dT) priming and reverse transcriptase. Moloney MLV reverse transcriptase available from Gibco/BRL, Bethesda, Md., or AMV reverse transcriptase available from Seikagaku America, Inc., St. Petersburg, Fla., are preferably employed.

Following reverse transcription, the cDNA clone is converted to double stranded DNA using conventional techniques and incorporated into a suitable vector. The experiments herein employed *E. coli* DNA polymerase I and ribonuclease H in the conversion to double stranded DNA.

Cloning of the cDNAs can be accomplished using any of the conventional techniques for joining double stranded DNA with an appropriate vector. The use of synthetic adaptors is particularly preferred, since it alleviates the possibility of cleavage of the cDNA with restriction enzyme prior to cloning. Using this method, non-self complementary, kinased adaptors are added to the DNA prior to ligation with the vector. Virtually any adaptor can be employed. As set forth in more detail in the examples below, non-self complementary BstXI adaptors are preferably added to the cDNA for cloning, for ligation into a pCDM8 vector prepared for cloning by digestion with BstXI.

Eukaryotic cDNA can be expressed when placed in the sense orientation in a vector that supplies an appropriate eukaryotic promoter and origin of replication and other elements including enhancers, splice acceptors and/or donor sequences and polyadenylation signals. The cDNAs of the present invention are placed in suitable vectors containing a strong eukaryotic promoter, an origin of replication functional in *E. coli*, an SV 40 origin of replication which allows growth in COS cells, and a cDNA insertion site. Suitable vectors include πH3 (Seed and Aruffo, *Proc, Natl. Acad. Sci.*, 84: 3365–3369 (1987)), πH3m (Aruffo and Seed, *Proc, Natl. Acad. Sci,.* 84: 8573–8577 (1987)), pCDM7 and pCDM8 (Seed, *Nature*, 329: 840–841 (1987), with the pCDM8 vector being particularly preferred (available commercially from Invitrogen, San Diego, Calif.).

Transfection of Host Cells and Screening for Novel B Lymphocyte Activation Antigens The thus prepared cDNA library is then cloned by expression cloning techniques. The basic expression cloning technique has been described by Seed and Aruffo, *Proc. Natl. Acad. Sci. USA*, 84: 3365–3369 (May 1987) and Aruffo and Seed, *Proc. Natl. Acad. Sci. USA*, 84: 8573–8577 (December 1987), although modifications to the technique may be necessary to successfully clone a novel B lymphocyte activation antigen.

According to one embodiment, plasmid DNA is introduced into a simian COS cell line (Gluzman, *Cell* 23: 175 (1981)) by known methods of transfection (e.g., DEAE-Dextran) and allowed to replicate and express the cDNA inserts. The transfectants expressing B7-1 antigen are depleted with an anti-B7-1 monoclonal antibody (e.g., 133 and B1.1) and anti-murine IgG and IgM coated immunomagnetic beads. Transfectants expressing B7-2 and B7-3 antigen were positively selected by reacting the fusion proteins with CTLA4-Ig and CD28-Ig followed by panning with anti-human Ig immunoglobulin coated plates. After panning, episomal DNA is recovered from the panned cells and transformed into a competent bacterial host, preferably *Escherichia coli*. Plasmid DNA is subsequently reintroduced into COS cells and the cycle of expression and panning repeated at least two times. After the final cycle, plasmid DNA is prepared from individual colonies, transfected into COS cells and analyzed for expression of novel B lymphocyte antigens by indirect immunofluorescence with CTLA4Ig and CD28Ig.

Sequencing of Novel B Lymphocyte Antigens

After cloning, plasmids are prepared from the clones strongly reactive with the CTLA4-Ig and sequenced. Any of the conventional sequencing techniques suitable for sequencing tracts of DNA about 1.0 kb) or larger can be employed.

As described in Example 4, a B7-2 clone (clone29) which contained an insert of 1.2 kilobases (kb) with a single long open reading frame of 987 nucleotides and approximately 27 nucleotides of 3' noncoding sequences (FIG. 8). The predicted amino acid sequence encoded by the open reading frame of the protein is shown below the nucleotide sequence in FIG. 8 (SEQ ID NO: 1). The encoded protein, B7-2, is predicted to be 329 amino acids in length (SEQ ID NO: 2). This protein sequence exhibits many features common to other type 1 Ig superfamily membrane proteins. Protein translation probably begins at the ATG codon (nucleotide 107) because this DNA sequence in this region shows features often found at eukaryotic translation initiation sites (Kozak, M. (1987) *Nucl. Acids Res.* 15: 8125–8148). The hydrophobic sequence at the amino terminus of the B7-2 protein (amino acids 1 to 23) has the characteristics of a secretory signal peptide; the method of von Heigne (*Nucl. Acids Res.* 14: 4683) predicts cleavage between the alanines at positions 23 and 24. Processing at this site would result in an unmodified B7-2 membrane bound protein of 306 amino acid having a molecular weight of approximately 36 kDa. This protein would consist of an approximately 220 amino acid extracellular Ig superfamily V and C like domains, a hydrophobic transmembrane domain of about 20 amino acids and a long cytoplasmic domain of approximately 60 amino acids. The homologies to the Ig superfamily are due to the two contiguous Ig-like domains in the extracellular region bound by the cysteines at positions 40 to 110 and 157 to 218. The extracellular domain also contains eight potential N-linked glycosylation sites. Comparison of both the nucleotide and protein sequences of B7-2 with the GenBank and EMBL databases yielded significant homology (~25%) with both human B7-1 and murine B7.

Cloning Novel B Lymphocyte Antigens From Other Mammalian Species

The present invention is not limited to human nucleic acid molecules and contemplates that novel B lymphocyte antigen homologues from other mammalian species that express B lymphocyte antigens can be cloned and sequenced using the techniques described herein. B lymphocyte antigens isolated for one species (e.g., humans) which exhibit cross-species reactivity may be used to modify T cell mediated immune responses in a different species (e.g., mice). Isolation of cDNA clones from other species can also be accomplished using human cDNA inserts, such as B7-2 cDNA, as hybridization probes.

Novel B lymphocyte activation antigen nucleic acid sequences from other species, such as the mouse, can be used to generate either transgenic animals or "knock out" animals which, in turn, are useful in the development and screening of therapeutically useful reagents. For example, murine cDNA or an appropriate sequence thereof can be used to clone for genomic B7-2 in accordance with established techniques and the genomic sequences used to generate transgenic animals that over-express B7-2. Methods for generating transgenic animals, particularly animals such as mice, have become conventional in the art and are described, for example, in U.S. Pat. Nos. 4,736,866 and 4,870,009. Typically, particular cells would be targeted for B7-2 transgene incorporation with tissue specific enhancers, which could lead to enhanced T cell proliferation and autoimmunity. Transgenic animals that include a copy of a B7-2 transgene introduced into the germ line of the animal at an embryonic stage can be used to examine the effect of increased B7 expression. Such animals can be used as tester animals for reagents thought to confer protection from, for example, autoimmune disease. In accordance with this facet of the invention, an animal is treated with the reagent and a reduced incidence of the disease, compared to untreated animals bearing the transgene would indicate a potential therapeutic intervention for the disease. Alternatively, the non-human homologues of B7-2 can be used to construct a B7-2 "knock out" animal which has a defective B7-2 gene. Such animals can be characterized for their ability to accept grafts, reject tumors and defend against infectious diseases.

Expression of B Lymphocyte Antigens

Host cells transfected to express novel B lymphocyte antigens are within the scope of the invention. The host cell may be any procaryotic or eucaryotic cell. For example, B7-2 protein may be expressed in bacterial cells such as *E. coli*, insect cells (baculovirus), yeast, or mammalian cells such as Chinese hamster ovary cells (CHO). Other suitable host cells may be found in Goeddel, (1990) supra or known to those skilled in the art.

For example, expression in eucaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *Embo J.* 6: 229–234), pMFa (Kurjan and Herskowitz, (1982) *Cell* 30: 933–943), pJRY88 (Schultz et al., (1987) *Gene* 54: 113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3: 2156–2165,) and the pVL series (Lucklow, V. A., and Summers, M. D., (1989) *Virology* 170: 31–39). Generally, COS cells (Gluzman, Y., (1981) *Cell* 23: 175–182) are used in conjunction with such vectors as pCDM 8 (Aruffo, A. and Seed, B., (1987) *Proc. Natl. Acad. Sci. USA* 84: 8573–8577) for transient amplification/expression in mammalian cells, while CHO (dhfr⁻ Chinese Hamster Ovary) cells are used with vectors such as pMT2PC (Kaufman et al. (1987), *EMBO J.* 6: 187–195) for stable amplification/expression in mammalian cells. A preferred cell line for production of recombinant protein is the NS0 myeloma cell line (a glutamine synthetase expression system.), available from Celltech Limited. Vector DNA can be introduced into mammalian cells via conventional techniques such as calcium phosphate or calcium chloride co-precipitation, DEAE-dextran-mediated transfection, lipofectin, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks. When used in mammalian cells, the expression vector's control functions are often provided by viral material. For example, commonly used promoters are derived from polyoma, Adenovirus 2, cytomegalovirus and most frequently, Simian Virus 40.

It is known that a small fraction of cells (about 1 out of $10^5$) typically integrate DNA into their genomes. In order to identify these integrants, a gene that contains a selectable marker (i.e. resistance to antibiotics) is generally introduced into the host cells along with the gene of interest. Preferred selectable markers include those which confer resistance to drugs, such as G418, hygromycin and methotrexate. Selectable markers may be introduced on the same plasmid as the gene of interest or may be introduced on a separate plasmid.

Cells containing the gene of interest are identified by drug selection; cells that have incorporated the selectable marker gene will survive, while the other cells die. The surviving cells can then be screened for production of novel B lymphocyte antigens by cell surface staining with ligands to the B cell antigens (e.g., CTLA4Ig and CD28Ig) and by radiolabeling the proteins with a labeled amino acid and immunoprecipitating the protein from the cell supernatant with an anti-B lymphocyte antigen monoclonal antibody.

Expression in procaryotes is most often carried out in *E. coli* with vectors containing constitutive or inducible promotors directing the expression of either fusion or non-fusion proteins. Fusion vectors usually add a number of $NH_2$ terminal amino acids to the expressed target gene. These $NH_2$ terminal amino acids often are referred to as a reporter group. Such fusion vectors usually serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

Inducible non-fusion expression vectors include pTrc (Amann et al., (1988) *Gene* 69: 301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant B7-2 expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid sequence of the B7-2 gene or other DNA to be inserted into an expression vector so that the individual codons for each amino acid would be those preferentially utilized in highly expressed *E. coli* proteins (Wada et al., (1992) *Nuc. Acids Res.* 20: 2111–2118). Such alteration of nucleic acid sequences of the invention could be carried out by standard DNA synthesis techniques.

Novel B lymphocyte antigens expressed in mammalian cells or otherwise can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22: 233–577 (1971)). Once purified, partially or to homogeneity, the recombinantly produced B lymphocyte antigens of the invention can be utilized in pharmaceutical compositions as described in more detail herein.

Modifications of Nucleic Acid and Amino Acid Sequences

It will be appreciated by those skilled in the art that other nucleic acid molecules coding for the novel B lymphocyte antigens can be isolated by the above process. Different cell lines can be expected to yield DNA molecules having different sequences of bases. Additionally, variations may exist due to genetic polymorphisms or cell-mediated modifications of the genetic material. Furthermore, the DNA sequence of B lymphocyte antigens can be modified by genetic techniques to produce proteins or peptides with altered amino acid sequences. Such sequences are considered within the scope of the present invention, where the expressed protein is capable of either enhancing or blocking activated T cell mediated immune responses and immune function.

A number of processes can be used to generate fragments, mutants and variants of the isolated DNA sequence. Small subregions or fragments of the nucleic acid encoding the B7-2 protein, for example 1–30 bases in length, can be prepared by standard, synthetic organic chemical means. The technique is also useful for preparation of antisense oligonucleotides and primers for use in the generation of larger synthetic fragments of B7-2 DNA.

Larger subregions or fragments of the genes encoding B lymphocyte antigens can be expressed as protein by synthesizing the relevant piece of DNA using the polymerase chain reaction (PCR) (Sambrook, Fritsch and Maniatis, 2 *Molecular Cloning; A Laboratory Manual*, Cold Spring Harbor, N.Y., (1989)), and ligating the thus obtained DNA into an appropriate expression vector. Using PCR, specific sequences of the cloned double stranded DNA are generated, cloned into an expression vector, and then assayed for CTLA4/CD28 binding activity. For example, to express a secreted (soluble) form of the human B7-2 polypeptide, a PCR product can be synthesized which does not include the transmembrane region of the protein, ligated into an appropriate expression vector and introduced into a host cell such as CHO, where the B7-2 polypeptide fragment is synthesized and secreted. The B7-2 polypeptide fragment can then readily be obtained from the culture media.

As used herein, the term "soluble B lymphocyte antigen" or "soluble B7-2 " means an amino acid sequence corresponding to the extracellular domain of the protein or any fragment thereof which does not include the cytoplasmic and/or transmembrane regions. Such polypeptides, when produced recombinantly in a host cell with the appropriate genetic regulatory elements (e.g., signal sequence), will be secreted freely into the medium, rather than anchored in the host cell membrane.

In another embodiment, mutations can be introduced into a gene by any one of a number of methods, including those for producing simple deletions or insertions, systematic deletions, insertions or substitutions of clusters of bases or substitutions of single bases, to generate variants of B lymphocyte antigen DNA. For example, changes in the B7-2 cDNA sequence such as amino acid substitutions or deletions are preferably obtained by site-directed mutagenesis. Site directed mutagenesis systems are well known in the art. Protocols and reagents can be obtained commercially from Amersham International PLC, Amersham, U.K.

Fragments, mutants and variants of B lymphocyte antigens that retain the ability to bind to their natural ligand(s) on T cells and either amplify or block activated T cell mediated immune responses, as evidenced by, for example, lymphokine production and/or T cell proliferation by T cells that have received a primary activation signal are considered within the scope of the invention. More specifically, B7-2 proteins and peptides that bind to T lymphocytes, for example $CD28^+$ cells, may be capable of delivering a costimulatory signal to the T lymphocytes, which, when transmitted in the presence of antigen and class II MHC, or other material capable of transmitting a primary signal to the T cell, results in activation of lymphokine genes within the T cell. Such B7-2 proteins can be considered to retain the essential characteristics of the B7-2 cell surface antigen. Alternatively, B7-2 proteins, particularly soluble, monomeric forms of the B7-2 protein, may retain the ability to bind to their natural ligand(s) on $CD28^+$ T cells but, perhaps because of insufficient cross-linking with the ligand, fail to deliver the secondary signal essential for enhanced lymphokine production and cell division. Such proteins, which provide a means to induce a state of anergy or tolerance in the cells, are also considered within the scope of the invention.

Screening the fragments, mutants or variants for those which retain characteristic B lymphocyte antigen activity as described herein can be accomplished using one or more of several different assays. For example, the fragments, mutants and variants can be screened for specific reactivity with an anti-B7-2 monoclonal antibody reactive with cell surface B7-2. Specifically, appropriate cells, such as CHO cells, can be transfected with the cloned variants and then analyzed for cell surface phenotype by indirect immunofluorescence and flow cytometry. Cell surface expression of the transfected cells is evaluated using a monoclonal antibody specifically reactive with cell surface B7-2. Production of secreted forms of B7-2 is evaluated using anti-B7-2 monoclonal antibody for immunoprecipitation.

Other, more preferred, assays take advantage of the functional characteristics of the B7-2 antigen. As previously set forth, the ability of T cells to synthesize lymphokines depends not only on occupancy or cross-linking of the T cell receptor for antigen ("the primary activation signal"), but also on the additional binding of a costimulatory signal, in this case, a B lymphocyte antigen, such as B7-2, B7-1 or B7-3. The binding of B7-2 to its natural ligand(s) on, for example, CD28 positive T cells, has the effect of transmitting a signal to the T cell that causes that cell to produce increased levels of lymphokines, particularly of interleukin-2 which in turn stimulates the proliferation of the T lymphocytes. Other assays for B7-2 function thus involve assaying for the synthesis of lymphokines, such as interleukin-2 or other novel and as yet undefined cytokines, and/or assaying for T cell proliferation by $CD28^+$ T cells which have received a primary activation signal.

In vitro, T cells can be provided with the first signal by anti-T3 monoclonal antibody (e.g. anti-CD3) or phorbol ester or, more preferably, by antigen in association with class II MHC. B7-2 function is assayed by adding a source of B7-2 (e.g., cells expressing B7-2 or a fragment, mutant or variant thereof or a secreted form of B7-2) and a primary activation signal such as antigen in association with Class II MHC and assaying the culture supernatant for interleukin-2, gamma interferon, or other undefined cytokine. Any one of several conventional assays for interleukin-2 can be employed, such as the assay described in *Proc. Natl. Acad. Sci. USA*, 86: 1333 (1989) the pertinent portions of which are hereby incorporated by reference. A kit for an assay for the production of interferon is available from Genzyme Corporation (Cambridge, Mass.). T cell proliferation can also be measured as described in the Examples below. B7-2 proteins and peptides that retain the characteristics of cell surface B7-2 will cause increased production of lymphokines, such as IL-2 and may also result in enhanced T cell proliferation when compared to a negative control in which the secondary signal is lacking.

The same basic functional assays can also be used to screen for B7-2 proteins that are incapable of delivering a costimulatory signal, but in the case of such proteins, addition of the B7-2 protein will not result in a marked increase in proliferation or lymphokine secretion by the T cells. The ability of such proteins to block the normal B7-2 costimulatory signal and induce a state of anergy can be determined using subsequent attempts at stimulation of the T cells with antigen presenting cells that express cell surface B cell activation antigen B7 and present antigen. If the T cells are unresponsive to the subsequent activation attempts, as determined by IL-2 synthesis and T cell proliferation, a state of anergy has been induced. See, e.g., Schwartz, *Science,* 1348, 1352–1354, for a model assay system that can used as the basis for an assay in accordance with the present invention.

It is also possible to modify the structure of a B lymphocyte antigen for such purposes as increasing solubility, enhancing therapeutic or prophylactic efficacy, or stability (e.g., shelf life ex vivo and resistance to proteolytic degradation in vivo). Such modified proteins are considered functional equivalents of the B lymphocyte antigens as defined herein. For example, the B7-2 protein can be modified so that it maintains the ability to co-stimulate T cell proliferation. Those residues shown to be essential to interact with the CTLA4/CD28 receptors on T cells can be modified by replacing the essential amino acid with another, preferably similar amino acid residue (a conservative substitution) whose presence is shown to enhance, diminish, but not eliminate, or not effect receptor interaction. In addition, those amino acid residues which are not essential for receptor interaction can be modified by being replaced by another amino acid whose incorporation may enhance, diminish, or not effect reactivity.

Another example of modification of a B lymphocyte antigen is substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the protein.

In order to enhance stability and/or reactivity, the B lymphocyte antigens can be modified to incorporate one or more polymorphisms in the amino acid sequence of the antigen resulting from any natural allelic variation. Additionally, D-amino acids, non-natural amino acids, or non-amino acid analogs can be substituted or added to produce a modified protein within the scope of this invention. Furthermore, the B7-2 protein can be modified using polyethylene glycol (PEG) according to the method of A. Sehon and co-workers (Wie et al., supra) to produce a protein conjugated with PEG. In addition, PEG can be added during chemical synthesis of the protein. Other modifications of the B7-2 protein include reduction/alkylation (Tarr in: *Methods of Protein Microcharacterization,* J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology,* W H Freeman, San Francisco, Calif. (1980), U.S. Pat. No. 4,939,239; or mild formalin treatment (Marsh (1971), *Int. Arch. of Allergy and Appl. Immunol.* 41: 199–215).

To facilitate purification and potentially increase solubility of a B lymphocyte antigen, it is possible to add an amino acid reporter group to the protein backbone. For example, hexa-histidine can be added to the protein for purification by immobilized metal ion affinity chromatography (Hochuli, E. et al., (1988) *Bio/Technology* 6: 1321–1325). In addition, to facilitate isolation of a CTLA4/CD28 binding counter-receptor protein free of irrelevant sequences, specific endoprotease cleavage sites can be introduced between the sequences of the reporter group and the protein or peptide. It may be necessary to increase the solubility of a B lymphocyte antigen by adding functional groups to the protein, or by omitting hydrophobic regions of the protein.

Uses of Nucleic Acid Sequences Encoding B Lymphocyte Antigens and Novel Proteins and Peptides The nucleic acid sequences of this invention are usefull diagnostically, for tracking the progress of disease, by measuring the activation status of B lymphocytes in biological samples. In accordance with this diagnostic assay, the nucleic acid sequences are labeled with a detectable marker, e.g., a radioactive, fluorescent, or biotinylated marker and used in a conventional dot blot or Northern hybridization procedure to probe mRNA molecules of total or poly(A+) RNAs from a biological sample.

In addition, the nucleic acid sequences and novel B lymphocyte antigens can be used in the development of therapeutic reagents having the ability to either upregulate (amplify) or downregulate (suppress) T cell mediated immune responses. For example, B7-2 proteins and peptides, including soluble, monomeric forms of the B7-2 antigen, that fail to deliver a costimulatory signal to T cells that have received a primary activation signal, can be used to block the B7-2 ligand(s) on T cells and thereby provide a specific means by which to induce tolerance in a subject. In contrast to the monomeric form, multivalent forms of B7-2, such as cell surface B7-2, retain the ability to transmit the costimulatory signal to the T cells, resulting in an increased secretion of lymphokines when compared to activated T cells that have not received the secondary signal In addition, fusion proteins comprising at least a portion of a B lymphocyte antigen (e.g., B7-2) fused to at least a portion of another B lymphocyte antigen (e.g., B7-1) can be used to modify T cell mediated immune responses. Alternatively, two separate B lymphocyte antigens (or therapeutically active portions thereof), for example, B7-2 protein and B7-1 protein, can be combined to upregulate or down regulate T cell mediated immune responses in a subject.

More specifically, given the structure and function of the novel B lymphocyte activation antigens disclosed herein, it is possible to upregulate or down regulate the function of a B lymphocyte antigen in a number of ways. Downregulating or preventing one or more B lymphocyte antigen functions, i.e., preventing high level lymphokine synthesis by activated T cells, should be useful in treating autoimmune diseases such as rheumatoid arthritis and multiple sclerosis and also in tissue and organ transplantation and graft versus host disease. For example, blockage of T cell function should result in reduced tissue destruction in tissue transplantation. Typically, in tissue transplants, rejection of the transplant is initiated by its recognition as foreign, followed by an immune reaction that destroys the transplant. The administration of a soluble, monomeric form of B7-2 alone or in conjuntion with a monomeric form of another B lymphocyte antigen (e.g., B7-1, B7-3) or blocking antibody, prior to transplantation can lead to the binding of the monomeric antigen(s) to its natural ligand(s) on T cells without transmitting the corresponding costimulatory signal and thus blocks the ligand(s) on T cells. Blocking B lymphocyte antigen function in this manner prevents T cell lymphokine synthesis and thus acts as an immunosuppressant. Moreover, the lack of costimulation may also be sufficient to induce T cell tolerance in a subject. It may also be necessary to block the function of a combination of B lymphocyte antigens to acheive sufficient immunosuppression or tolerance in a subject. For example, it may be desirable to block the function of both B7-2 and B7-1, B7-2 and B7-3, B7-1 and B7-3 or B7-2, B7-1 and B7-3 by administering a soluble form of each of these antigens prior to transplantation or in the treatment of an autoimmune disease.

In addition, in the acquired immune deficiency syndrome (AIDS), viral replication is stimulated by T cell activation. Blocking B7-2 function could lead to a lower level of viral replication and thereby ameliorate the course of AIDS. In addition, it may also be necessary to block the function of a combination of B lymphocyte antigens i.e., B7-1, B7-2 and B7-3. Surprisingly, HTLV-I infected T cells express B7-1 and B7- 2. This expression may be important in the growth of HTLV-I infected T cells and the blockage of B7-1 function together with the function of B7-2 and/or B7-3 may slow the growth of HTLV-I induced leukemias.

One method of preventing the function of a B lymphocyte antigen is through the use of an antisense or triplex oligonucleotides. For example, an oligonucleotide complementary to the area around the B7-1, B7-2 or B7-3 translation initiation site, (e.g., for B7-1, TGGCCCATGGCTTCAGA (SEQ ID NO: 20), nucleotides 326–309 and for B7-2, GCCAAAATGGATCCCCA)(SEQ ID NO: 21), can be synthesized. One or more antisense oligonucleotides can be added to cell media, typically at 200 μg/ml, or administered to a patient to prevent the synthesis of B7-1, B7-2 and/or B7-3. The antisense oligonucleotide is taken up by cells and hybridizes to the appropriate B lymphocyte antigen mRNA to prevent translation. Alternatively, an oligonucleotide which binds double-stranded DNA to form a triplex construct to prevent DNA unwinding and transcription can be used. As a result of either, synthesis of one or more B lymphocyte antigens is blocked.

The proteins or polypeptides produced from the nucleic acid molecules of the present invention may also be useful in the construction of therapeutic agents which block B lymphocyte antigens. For example, as described, secreted forms of B lymphocyte activation antigen can be constructed by standard genetic engineering techniques. By linking soluble B7-1, B7-2 or B7-3 to a toxin such as ricin, an agent capable of preventing T cell activation would be made. Infusion of one or a combination of immunotoxins, e.g., B7-2-ricin, into a patient would result in the death of T cells, particularly of activated T cells that express higher amounts of CD28 and CTLA4. Soluble B7-2 in a monovalent form alone may be useful in blocking B7-2 function, as described above, in which case a carrier molecule may also be employed.

Upregulation of a B lymphocyte antigen function may also be useful in therapy. For example, viral infections are cleared primarily by cytolytic T cells. In accordance with the present invention, it is believed that the interaction of B7-1 and, thus, B7-2 and B7-3 with their natural ligand(s) on T cells results in an increase in the cytolytic activity of at least some T cells. It is also believed that B7-1, B7-2 and B7-3 are involved in the initial activation and generation of CD8+ cytotoxic T cells. The addition of soluble B7-2, alone, in combination with another B lymphocyte antigen in a multi-valent form to stimulate T cell activity through the costimulation pathway would thus be therapeutically useful in situations where more rapid or thorough clearance of virus would be beneficial. These would include viral skin diseases such as Herpes simplex or shingles, in which cases the multi-valent soluble B7-2 or combination of B7-2 and/or B7-1 and/or B7-3 is delivered topically to the skin. In addition, systemic viral diseases such as influenza, the common cold, and encephalitis might be alleviated by the administration of B lymphocyte antigens systemically.

Alternatively, therapeutic intervention with the B lymphocyte antigens described herein and peptides can involve removal of certain of a patients' activated T cells and costimulating the cells with B7-2 alone or in combination with B7-1 and/or B7-3 in vitro.

In another application, upregulation or enhancement of B lymphocyte antigen function may be useful in the induction of tumor immunity. Tumor cells (e.g., sarcoma, melanoma, lymphoma, leukemia, neuroblastoma, carcinoma) transfected with a nucleic acid encoding at least one B lymphocyte antigen, such as B7-2, can be administered to a subject to overcome tumor-specific tolerance in the subject. If desired, the tumor cell can be transfected to express at least a portion of a combination of B lymphocyte activation antigens (e.g., B7-1, B7-2, B7-3). For example, tumor cells obtained from a patient can be transfected ex vivo with an expression vector directing the expression of at least a portion of the B7-2 lymphocyte antigen alone, or in conjuction with the B7-1 and/or the B7-3 antigen, or portions thereof. The transfected tumor cells are returned to the patient to result in expression of the B lymphocyte antigen (s) described herein or portions thereof on the surface of the transfected cell. Alternatively, gene therapy techniques can be used to target a tumor cell for transfection in vivo. The presence of the B lymphocyte antigen(s) on the surface of the tumor cell provides the necessary costimulation signal to T cells to induce a T cell mediated immune response against the transfected tumor cells. In addition, tumor cells which lack MHC class II molecules, or which fail to express sufficient amounts of MHC class II molecules, can be transfected with nucleic acid encoding all or a portion of (e.g., a cytoplasmic-domain truncated portion) of an MHC class II $\alpha$ chain protein and an MHC class II $\beta$ chain protein to thereby express MHC class II proteins on the cell surface. Expression of class II MHC in conjunction with a B lymphocyte anigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a gene encoding a B lymphocyte antigen to induce tumor specific immunity. Expression of B7-1 by B7 negative murine tumor cells has been shown to induce T cell mediated specific immunity accompanied by tumor rejection and prolonged protection to tumor challenge in mice (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690). Thus, the induction of a T cell mediated immune response in a human subject may be sufficient to overcome tumor-specific tolerance in the subject.

The proteins and peptides of the present invention are administered to subjects in a biologically compatible form suitable for administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of at least one B lymphocyte antigen as described herein can be in any pharmacological form including a therapeutically active amount of B7-2 protein alone or in combination with another B lymphocyte antigen and a pharmaceutically acceptable carrier. Administration of the therapeutic compositions of the present invention to a subject can be carried out using known procedures, at dosages and for periods of time effective to acheive the desired result. For example, a therapeutically active amount of B7-2 protein may vary according to factors such as the age, sex, and weight of the individual, and the ability of the B7-2 protein to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (i.e., B lymphocyte antigen) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. If the active compound is administered by injection, for example, about 1 $\mu$g–3 mg and preferably from about 20 $\mu$g–500 $\mu$g of active compound (e.g., B7-2 protein) per dosage unit may be administered.

To administer B7-2 protein by other than parenteral administration, it may be necessary to coat the protein or peptide with, or co-administer the protein with, a material to prevent its inactivation. For example, B7-2 protein may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol* 7: 27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearite and gelatin.

Sterile injectable solutions can be prepared by incorporating active compound (e.g., B7-2 protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., protein) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Another application of the B lymphocyte antigen of the invention (e.g., B7-1, B7-2 and B7-3) is the use of one or more of these proteins (or portion thereof) in screening assays to inhibit binding of a B lymphocyte antigen, such as B7-2, with the appropriate T cell ligand (e.g. CTLA4, CD28) to discover as yet undefined molecules which are inhibitors of ligand binding and/or are involved in intracellular signaling of T cell costimulation following ligand binding.

The novel B lymphocyte antigens described herein can also be used to produce antibodies specifically reactive with the B lymphocyte antigen. For example, antibodies reactive with the B7-2 antigen can be used to isolate the naturally-occurring or native form of B7-2 or to block B7-2 function. For example, by using isolated B7-2 protein based on the cDNA sequence of B7-2, anti-protein/anti-peptide antisera or monoclonal antibodies can be made using standard methods. A mammal, (e.g., a mouse, hamster, or rabbit) can be immunized with an immunogenic form of the protein antigen (e.g, B7-2) which elicits an antibody response in the mammal. Techniques for conferring immunogenicity on a protein antigen include conjugation to carriers or other techniques well known in the art. For example, the protein antigen can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256: 495–497) as well as other techniques such as the human B-cell hybridoma technique (Kozbar et al., *Immunol. Today* (1983) 4: 72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246: 1275). Hybridoma cells can be screened immunochemically for production of antibodies specifically reactive with the protein antigen and monoclonal antibodies isolated.

The term antibody as used herein is intended to include fragments thereof which are also specifically reactive with the novel B lymphocyte antigens described herein or portion thereof. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-B lymphocyte activation antigen (i.e., B7-2, B7-3) portion.

When antibodies produced in non-human subjects are used therapeutically in humans, they are recognized to varying degrees as foreign and an immune response may be generated in the patient. One approach for minimizing or eliminating this problem, which is preferably to general immunosuppression, is to produce chimaeric antibody derivatives, i.e. antibody molecules that combine a non-human animal variable region and a human constant region. Chimaeric antibody molecules can include, for example, the antigen binding domain from an antibody of a mouse, rat, or other species, with human constant regions. A variety of approaches for making chimaeric antibodies have been described and can be used to make chimaeric antibodies containing the immunoglobulin variable region which recognizes the gene product of the novel B lymphocyte antigens of the invention. See, for example, Morrison et al., *Proc. Natl. Acad Sci. U.S.A.* 81: 6851 (1985); Takeda et al., *Nature* 314: 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimaeric antibodies specifically reactive with the B lymphocyte antigens described herein can be further humanized by producing human constant region chimaeras, in which even parts of the variable regions, especially the conserved for framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.,* 80: 7308–7312 (1983); Kozbor et al., *Immunology Today,* 4: 7279 (1983); Olsson et al., *Meth. Enzymol.,* 92: 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

A further aspect of this invention pertains to a purified protein consisting essentially of a novel B lymphocyte antigen. The term purified B lymphocyte antigen or purified B7-2 protein is defined as the naturally-occurring or native B lymphocyte antigen essentially free of all other proteins. Purified B7-2 protein can be isolated from activated B lymphoctes by, for example, affinity chromatography with an antibody of the invention as described herein such as an antibody specifically reactive with the recombinant or synthetic B7-2 protein of the invention.

This invention is further illustrated by the following examples which should not be construed as limiting. The contents of all references and published patent applications cited throughout this application are hereby incorporated by reference.

The following methodology was used in Examples 1, 2 and 3.

Methods and Materials

A. Cells

Mononuclear cells were isolated by Ficoll-Hypaque density gradient centrifugation from single cell suspensions of normal human spleens and were separated into E− and E+ fractions by rosetting with sheep red blood cells (Boyd, A. W., et al. (1985) *J. Immunol.* 134, 1516). B cells were purified from the E− fraction by adherence of monocytes on plastic and depletion of residual T, natural killer cells (NK) and residual monocytes by two treatments with anti-MsIgG and anti-MsIgM coated magnetic beads (Advanced Magnetics, Cambridge, Mass.), using monoclonal antibodies: anti-CD4, -CD8, -CD11b, -CD14 and -CD16. CD4+ T cells were isolated from the E+ fraction of the same spleens after adherence on plastic and depletion of NK, B cells and residual monocytes with magnetic beads and monoclonal antibodies: anti-CD20, -CD11b, -CD8 and -CD16. CD28+ T cells were identically isolated from the E+ fraction using anti-CD20, -CD11b, -CD14 and -CD16 monoclonal antibodies. The efficiency of the purification was analyzed by indirect immunofluorescence and flow cytometry using an EPICS flow cytometer (Coulter). B cell preparations were >95% CD20+, <2% CD3+, <1% CD14+. CD4+ T cell preparations were >98% CD3+, >98% CD4+, <1% CD8+, <1% CD20+, <1% CD14+. CD28+ T cell preparations were >98% CD3+, >98% CD28 +, <1% CD20+, <1% CD14+.

B. Monoclonal Antibodies and Fusion Proteins

Monoclonal antibodies were used as purified Ig unless indicated otherwise: anti-B7: 133, IgM is a blocking antibody and has been previously described (Freedman, A. S. et al. (1987) *Immunol.* 137, 3260–3267); anti-B7: B1.1, IgG1 (RepliGen Corp. Cambridge, Mass.) (Nickoloff, B., et al (1993) *Am. J Pathol.* 142, 1029–1040) is a non-blocking monoclonal antibody; BB-1: IgM is a blocking antibody (Dr. E. Clark, University of Washington, Seattle, Wash.) (Yokochi, T., et al. (1982) *J. Immunol.* 128, 823–827); anti-CD20: B1, IgG2a (Stashenko, P., et al.(1980) *J. Immunol.* 125, 1678–1685); anti-B5: IgM (Freedman, A., et al. (1985) *J. Immunol.* 134, 2228–2235); anti-CD8: 7PT 3F9, IgG2a; anti-CD4: 19Thy5D7, IgG2a; anti-CD11b: Mol, IgM and anti-CD14: Mo2, IgM (Todd, R, et al. (1981) *J. Immunol.* 126, 1435–1442); anti-MHC class II: 9–49, IgG2a (Dr R. Todd, University of Michigan, Ann Arbor) (Todd, R. I., et al. (1984) *Hum Immunol.* 10, 23–40; anti-CD28: 9.3, IgG2a (Dr C. June, Naval Research Institute, Bethesda) (Hansen, J. A., et al. (1980) *Immunogenetics.* 10, 247–260); anti-CD16: 3G8, IgG1 (used as ascites) (Dr J. Ritz, Dana-Farber Cancer Institute, Boston); anti-CD3: OKT3, IgG2a hybridoma was obtained from the American Type Culture Collection and the purified monoclonal antibody was adhered on plastic plates at a concentration of 1 $\mu$g/ml; anti-CD28 Fab fragments were generated from the 9.3 monoclonal antibody, by papain digestion and purification on a protein A column, according to the manufacturer's instructions (Pierce, Rockford, Ill.). Human CTLA4 fusion protein (CTLA4-Ig) and control fusion protein (control-Ig) were prepared as previously described (Gimmi, C. D., et al. (1993) *Proc. Natl. Acad. Sci USA* 90: 6586–6590); Boussiotis, V., et al *J. Exp. Med.* (accepted for publication)).

C. CHO Cell Transfection

B7-1 transfectants (CHO-B7) were prepared from the B7-1 negative chinese hamster ovary (CHO) cell line, fixed with paraformaldehyde and used as previously described (Gimmi, C. D., et al. *Proc. Natl. Acad. Sci USA* 88, 6575–6579).

D. In Vitro B Cell Activation and Selection of B7+ and B7− Cells

Splenic B cells were cultured at $2 \times 10^6$ cells/ml in complete culture media, {RPMI 1640 with 10% heat inactivated fetal calf serum (FCS), 2 mM glutamine, 1 mM sodium pyruvate, penicillin (100 units/ml), streptomycin sulfate (100 $\mu$g/ml) and gentamycin sulfate (5 $\mu$g/ml)}, in tissue culture flasks and were activated by crosslinking of sIg with affinity purified rabbit anti-human IgM coupled to Affi-Gel 702 beads (Bio-Rad), Richmond, Calif.) (Boyd, A. W., et al., (1985) *J. Immunol.* 134,1516) or by crosslinking of MHC class II with 9–49 antibody coupled to Affi-Gel 702 beads. B cells activated for 72 hours, were used as total activated B cell populations or were indirectly stained with anti-B7 (B1.1) monoclonal antibody and fluorscien isothiocyanate (FITC) labeled goat anti-mouse immunoglobulin (Fisher, Pittsburgh, Pa.), and fractionated into B7+ and B7− populations by flow cytometric cell sorting (EPICS Elite flow cytometer, Coulter).

E. Immunoflouorescence and Flow Cytometry

For surface phenotype analysis populations of B cells activated by either sIg or MHC class II crosslinking for 6, 12, 24, 48, 72 and 96 hours were stained with either anti-B7 (133), BB-1 monoclonal antibodies, control IgM antibody, CTLA4-Ig or control-Ig. Cell suspensions were stained by two step indirect membrane staining with 10 $\mu$g/ml of primary monoclonal antibody followed by the appropriate secondary reagents. Specifically, immunoreactivity with anti-B7 (133) and BB-1 monoclonal antibodies was studied by indirect staining using goat anti-mouse Ig or immunoglobulin FITC (Fisher) as secondary reagent and immunoreactivity with fusion proteins was studied using biotinylated CTLA4-Ig or biotinylated control-Ig and streptavidin-phycoerythrin as secondary reagent. PBS containing 10% AB serum was used as diluent and wash media. Cells were fixed with 0.1% paraformaldehyde and analyzed on a flow cytometer (EPICS Elite Coulter).

F. Proliferation Assay

T cells were cultured at a concentration of $1\times10^5$ cells per well in 96-well flat bottom microtiter plate at 37° C. for 3 days in 5% $CO_2$. Syngeneic activated B cells (total B cell population or B7+ and B7− fractions) were irradiated (2500 rad) and added into the cultures at a concentration of $1\times10^5$ cells per well. Factors under study were added to the required concentration for a total final volume of 200 $\mu$l per well. When indicated, T cells were incubated with anti-CD28 Fab (final concentration of 10 $\mu$g/ml), for 30 minutes at 4° C., prior to addition in experimental plates. Similarly, CHO-B7 or B cells were incubated with CTLA4-Ig or control-Ig (10 $\mu$g/ml) for 30 minutes at 4° C. Thymidine incorporation as an index of mitogenic activity, was assessed after incubation with 1 $\mu$Ci (37kBq) of {methyl-$^3$H} thymidine (Du Pont, Boston, Mass.) for the last 15 hours of the culture. The cells were harvested onto filters and the radioactivity on the dried filters was measured in a Pharmacia beta plate liquid scintillation counter.

G. IL-2 and IL-4 Assay

IL-2 and IL-4 concentrations were assayed by ELISA (R&D Systems, Minneapolis, Minn. and BioSource, Camarillo, Calif.) in culture supernatants collected at 24 hours after initiation of the culture.

Example 1: Expression of a Novel CTLA4 Ligand on Activated B Cells Which Induces T Cell Proliferation Since crosslinking surface Ig induces human resting B cells to express B7-1 maximally (50–80%) at 72 hours, the ability of activated human B lymphocytes to induce submitogenically activated T cells to proliferate and secrete IL-2 was determined. FIG. 1 depicts the costimulatory response of human splenic CD4+ T cells, submitogenically activated with anti-CD3 monoclonal antibody, to either B7-(B7-1-) transfected CHO cells (CHO-B7) or syngeneic splenic B cells activated with anti-Ig for 72 hours. Submitogenically activated CD4+ T cells proliferated and secreted high levels of IL-2 in response to B7-1 costimulation provided by CHO-B7 (panel a). Both proliferation and IL-2 secretion were totally inhibited by blocking the B7-1 molecule on CHO cells with either anti-B7-1 monoclonal antibody or by a fusion protein for its high affinity receptor, CTLA4. Similarly, proliferation and IL-2 secretion were abrogated by blocking B7-1 signalling via CD28 with Fab anti-CD28 monoclonal antibody. Control monoclonal antibody or control fusion protein had no effect. Nearly identical costimulation for proliferation and IL-2 secretion was provided by splenic B cells activated with anti-Ig for 72 hours (panel b). Though anti-B7-1 monoclonal antibody could completely abrogate both proliferation and IL-2 secretion delivered by CHO-B7, anti-B7-1 monoclonal antibody consistently inhibited proliferation induced by activated B cells by only 50% whereas IL-2 secretion was totally inhibited. In contrast to the partial blockage of proliferation induced by anti-B7-1 monoclonal antibody, both CTLA4-Ig and Fab anti-CD28 monoclonal antibody completely blocked proliferation and IL-2 secretion. Identical results were obtained when the responding T cell population was CD28+ T cells and when PMA was used to deliver the first submitogenic signal rather than anti-CD3 (data not shown). These results are consistent with the hypothesis that activated human B cells express one or more additional CTLA4/CD28 ligands which can induce T cell proliferation without detectable IL-2 secretion.

Example 2: Activated Human Splenic B Cells Express CTLA4 Ligand(s) Distinct from B7-1

Figure 2B:
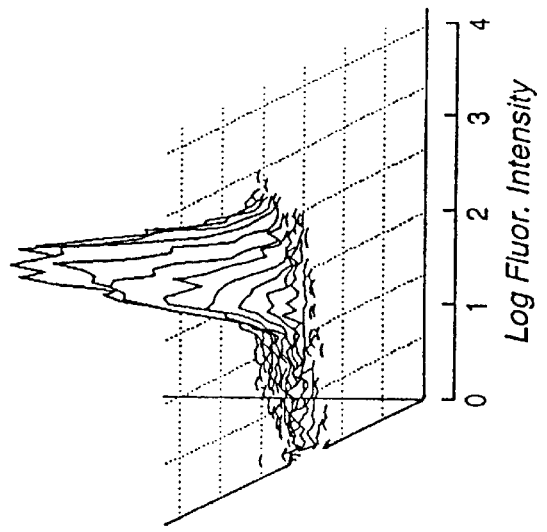
Figure 2C:
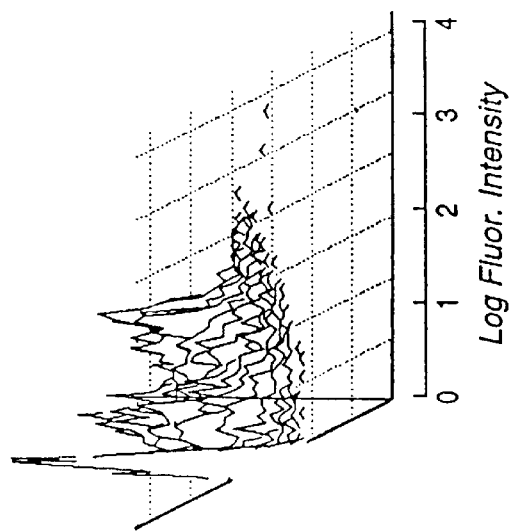

In light of the above observations, whether other CTLA4 binding counter-receptors were expressed on activated B cells was determined. To this end, human splenic B cells were activated for 72 hours with anti-Ig and then stained with an anti-B7-1 monoclonal antibody (B1.1) which does not inhibit B7-1 mediated costimulation. B7+ and B7− fractions were isolated by flow cytometric cell sorting. The resulting post-sort positive population was 99% B7+ and the post-sort negative population was 98% B7− (FIG. 2).

To examine the costimulatory potential of each population, human splenic CD4+ T cells were submitogenically stimulated with anti-CD3 monoclonal antibody in the presence of irradiated B7+ or B7− anti-Ig activated (72 hours) splenic B cells. B7+ B cells induced anti-CD3 activated T cells to proliferate and secrete IL-2 (FIG. 3a) but not IL-4 (data not shown). As was observed with the unfractionated activated B cell population, anti-B7-1 monoclonal antibody (133) inhibited proliferation only 50% but consistently abrogated IL-2 secretion. As above, CTLA4-Ig binding or blockade of CD28 with Fab anti-CD28 monoclonal antibody completely inhibited both proliferation and IL-2 secretion. Control monoclonal antibody and control-Ig were not inhibitory. In an attempt to identify other potential CTLA4/CD28 binding costimulatory ligand(s) which might account for the residual, non-B7 mediated proliferation delivered by B7+ B cells., the effect of BB-1 monoclonal antibody on proliferation and IL-2 secretion was examined. As seen, BB-1 monoclonal antibody completely inhibited both proliferation and IL-2 secretion (FIG. 3a). FIG. 3b displays the costimulatory potential of B7− activated human splenic B cells. Irradiated B7− activated (72 hr) B cells could also deliver a significant costimulatory signal to submitogenically activated CD4+ lymphocytes. This costimulation was not accompanied by detectable IL-2 (FIG. 3b) or IL-4 (data not shown) accumulation and anti-B7-1 monoclonal antibody did not inhibit proliferation. However, CTLA4-Ig, Fab anti-CD28 monoclonal antibody, and BB-1 monoclonal antibody all completely inhibited proliferation.

Figure 4:
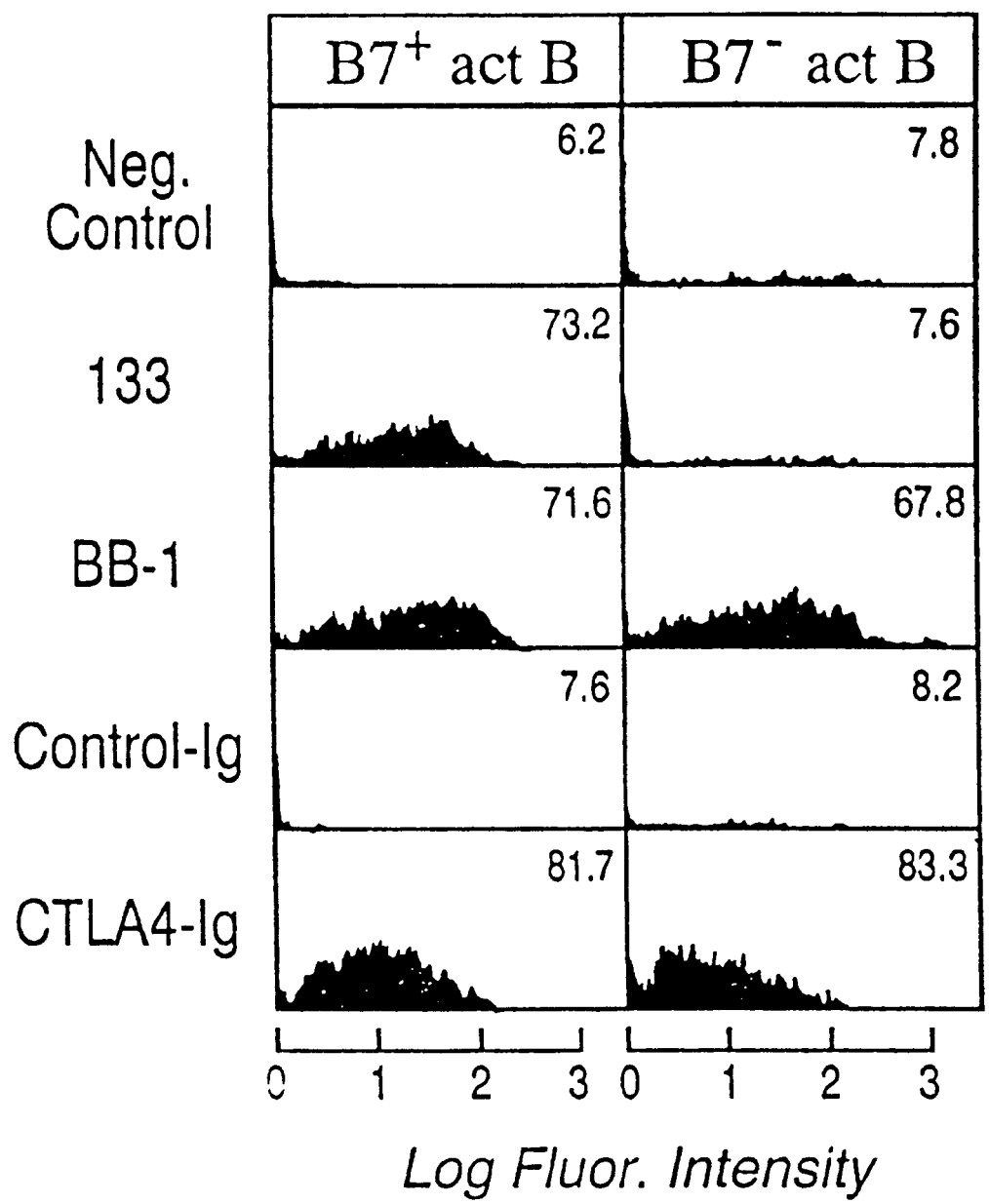
FIG. 4 is a graphic representation of the cell surface expression of the three CTLA4Ig binding proteins (B7-1, B7-2 and B7-3). These CTLA4/CD28 ligands can be distinguished on the basis of their temporal expression after B cell activation and their reactivity with CTLA4Ig and anti-B7 monoclonal antibodies. B7-1 (mAb 133), B7-1 and B7-3 (mAb BB-1) and B7-1, B7-2 and B7-3 (CTLA4Ig) binding counter-receptors on fractionated B7-1 positive and B7-1 negative activated B lymphocytes. The results are representative of five experiments.

Phenotypic analysis of the B7+ and B7− activated splenic B cells confirmed the above functional results. As seen in FIG. 4, B7+ activated splenic B cells stained with anti-B7-1 (133) monoclonal antibody, BB-1 monoclonal antibody, and bound CTLA4-1g. In contrast, B7− activated splenic B cells did not stain with anti-B7-1 (133) monoclonal antibody but did stain with BB-1 monoclonal antibody and CTLA4-Ig. These phenotypic and functional results demonstrate that both B7+ and B7− activated (72 hours) human B lymphocytes express CTLA4 binding counter-receptor(s) which: 1) can induce submitogenically activated T cells to proliferate without detectable IL-2 secretion; and 2) are identified by the BB-1 monoclonal antibody but not anti-B7-1 monoclonal antibody.

Figure 5:
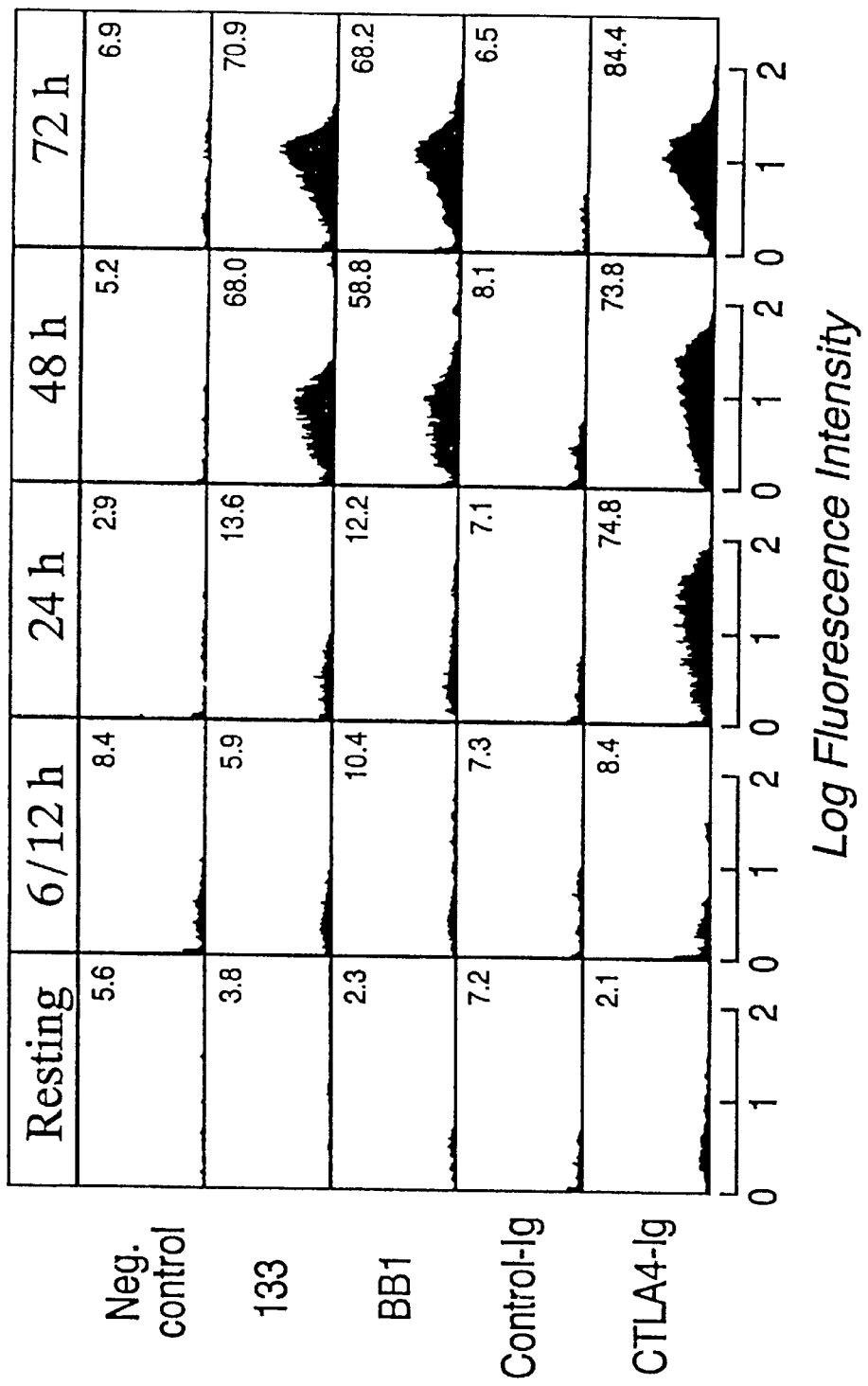
FIG. 5 is a graphic representations of temporal surface expression of B7-1 (CTLA4Ig and mAbs BB-1 and 133), B7-3 (CTLA4 and mAb BB1) and B7-2 (CTLA4-Ig) counter-receptors on splenic B cells activated by sIg crosslinking. Following activation, cells were harvested and binding of anti-B7 (CTLA4Ig and mAbs BB-1 and 133), anti-B7-3 (CTLA4 and mAb BB-1) and B7-2 (CTLA4-Ig) were assessed. The results are representative of 25 experiments for B7 and BB-1 binding and five experiments for CTLA4-Ig binding.
Figure 6:
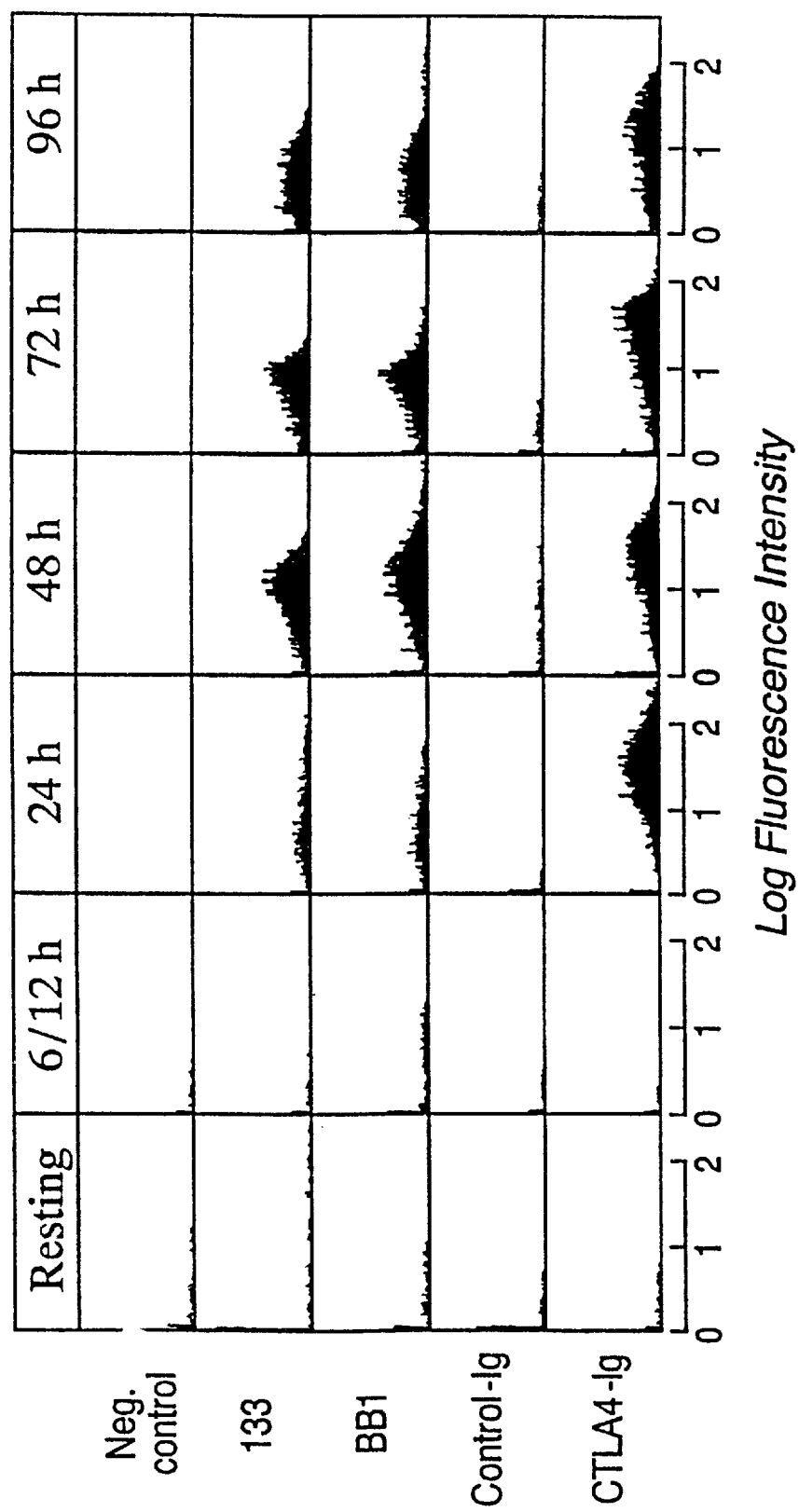
FIG. 6 is a graphic representation of temporal surface expression of B7-1 (CTLA4Ig and mAbs BB-1 and 133), B7-3 (CTLA4Ig and mAb BB1) and B7-2 (CTLA4-Ig) counter-receptors on splenic B cells activated by MHC class II crosslinking. Following activation, cells were harvested and binding of anti-B7 (CTLA4Ig and mAbs BB-1 and 133), anti-B7-3 (CTLA4 and mAb BB-1) and B7-2 (CTLA4-Ig) were examined. Results are representative of 25 experiments for B7 and BB1 monoclonal antibody binding and five experiments for CTLA4-Ig binding.

Example 3: Three Distinct CTLA4/CD28 Ligands Are Expressed Following Human B Cell Activation To determine the sequential expression of CTLA4 binding counter-receptors following activation, human splenic B cells were activated by crosslinking of either surface Ig or MHC class II and the expression of B7-1, B7-3 and B7-2 binding proteins were examined by flow cytometric analysis. Ig or MHC class II crosslinking induced similar pattern of CTLA4-Ig binding (B7-2), B7-1, and B7-3 expression (FIGS. 5 and 6). Prior to 24 hours, none of these molecules are expressed. At 24 hours post-activation, the majority of cells express a protein that binds CTLA4-Ig (B7-2), however, fewer than 20% express either B7-1 or B7-3. Crosslinking of MHC class II induces maximal expression and intensity of B7-1 and B7-3 at 48 hours whereas crosslinking of Ig induces maximal expression at 72 hours and expression declines thereafter. These results suggest that an additional CTLA4 binding counter-receptor is expressed by 24 hours and that the temporal expression of the distinct B7-1 and B7-3 proteins appears to coincide.

A series of experiments was conducted to determine whether the temporal expression of CTLA4 binding counter-receptors differentially correlated with their ability to costimulate T cell proliferation and/or IL-2 secretion. Human splenic CD4+ T cells submitogenically stimulated with anti-CD3 were cultured for 72 hours in the presence of irradiated human splenic B cells that had been previously activated in vitro by sIg crosslinking for 24, 48, or 72 hours. IL-2 secretion was assessed at 24 hours and proliferation at 72 hours. As seen in FIG. 7a, 24 hour activated B cells provided a costimulatory signal which was accompanied by modest levels of IL-2 production, although the magnitude of proliferation was significantly less than observed with 48 and 72 hours activated human B cells (note differences in scale for $^3$H-Thymidine incorporation). Neither proliferation nor IL-2 accumulation was inhibited by anti-B7-1 (133) or BB-1. In contrast with CTLA4-Ig and Fab anti-CD28 monoclonal antibody totally abrogated proliferation and IL-2 accumulation. B cells activated for 48 hours, provided costimulation which resulted in nearly maximal proliferation and IL-2 secretion (FIG. 7b). Here, anti-B7-1 (133) monoclonal antibody, inhibited proliferation approximately 50% but totally blocked IL-2 accumulation. BB-1 monoclonal antibody totally inhibited both proliferation and IL-2 secretion. As above, CTLA4-Ig and Fab anti-CD28 also totally blocked proliferation and IL-2 production. Finally, 72 hour activated B cells induced T cell response (previously discussed) identical to that induced by 48 hour activated B cells. Similar results are observed if the submitogenic signal is delivered by phorbol myristic acid (PMA) and if the human splenic B cells are activated by MHC class II rather than Ig crosslinking. These results indicate that there are three CTLA4 binding molecules that are temporarily expressed on activated B cells and each can induce submitogenically stimulated T cells to proliferate. Two of these molecules, the early CTLA4 binding counter-receptor (B7-2) and B7-1 (133) induce IL-2 production whereas B7-3 induces proliferation without detectable IL-2 production.

Previous studies provided conflicting evidence whether the anti-B7 monoclonal antibody, 133 and monoclonal antibody BB-1 identified the same molecule (Freedman, A. S. et al. (1987) Immunol. 137, 3260–3267; Yokochi, T., et al. (1982) J. Immunol. 128, 823–827; Freeman, G. J., et al. (1989) J. Immunol. 143, 2714–2722.). Although both monoclonal antibodies identified molecules expressed early following human B-cell activation, several reports suggested that B7 (B7-1) and the molecule identified by monoclonal antibody BB-1 were distinct since they were differentially expressed on cell lines and B cell neoplasms (Freedman, A. S. et al. (1987) Immunol 137, 3260–3267; Yokochi, T., et al. (1982) J. Immunol 128, 823–827; Freeman, G. J., et al. (1989) J. Immunol 143, 2714–2722; Clark, E and Yokochi, T. (1984) Leukocyte Typing, 1st International References Workshop. 339–346; Clark, E., et al. (1984) Leukocyte Typing, 1st International References Workshop. 740.). In addition, immunoprecipitation and Western Blotting with these IgM monoclonal antibodies suggested that they identified different molecules (Clark, E and Yokochi, T. (1984) Leukocyte Typing, 1st International References Workshop. 339–346; Clark, E., et al. (1984) Leukocyte Typing, 1st International References Workshop. 740.). The original anti-B7 monoclonal antibody, 133, was generated by immunization with anti-immunoglobulin activated human B lymphocytes whereas the BB-1 monoclonal antibody was generated by immunization with a baboon cell line. Thus, the BB-1 monoclonal antibody must identify an epitope on human cells that is conserved between baboons and humans. Following the molecular cloning and expression of the human B7 gene (B7-1), we demonstrated that B7 transfected COS cells identically stained with the anti-B7 (133) and BB-1 monoclonal antibodies and that they both precipitated the identical broad molecular band (44–54 kD) strongly suggesting that they identified the same molecule (Freeman, G. J., et al. (1989) J Immunol. 143, 2714–2722). This observation was somewhat disturbing since the gene encoding the molecule identified by the BB-1 monoclonal antibody had been previously mapped to chromosome 12 (Katz, F. E., et al. (1985) Eur. J. Immunol 103–6), whereas the B7 gene was located by two groups on chromosome 3 (Freeman, G. J., et al. (1992) Blood 79, 489–494; Selvakumar, A., et al. (1992) Immunogenetics 36, 175–181.). Subsequently, additional discrepancies between the phenotypic expression of B7 (B7-1) and the molecule identified by the BB-1 monclonal antibody were noted. BB-1 monoclonal antibody stained thymic epithelial cells (Turka, L. A., et al. (1991) J. Immunol. 146, 1428–36; Munro, J. M., et al. Blood submitted.) and keratinocytes (Nickoloff, B., et al (1993) Am. J Pathol. 142, 1029–1040; Augustin, M., et al. (1993) J. Invest. Dermatol. 100, 275–281.) whereas anti-B7 did not. Recently, Nickoloff et al. (Augustin, M., et al. (1993) J. Invest. Dermatol 100, 275–281) reported discordant expression of the molecule identified by the BB-1 monoclonal antibody and B7 on keratinocytes using a BB-1 and anti-B7 (B1.1 and 133) monoclonal antibodies. They also demonstrated that these BB-1 positive cells did not express B7 mRNA yet bound CD28 transfected COS cells providing further support for the existence of a distinct protein which binds monoclonal antibody BB-1.

Our present findings confirm that there is an additional CTLA4 counter-receptor identified by the BB-1 monoclonal antibody, B7-3, and that this protein appears to be functionally distinct from B7-1 (133). Although the expression of B7-1 and B7-3 following B cell activation appears to be concordant on B7 positive B cells, these studies demonstrate that the B7-3 molecule is also expressed on B7 negative activated B cells. More importantly, the B7-3 molecule appears to be capable of inducing T cell proliferation without detectable IL-2 or IL-4 production. This result is similar to the previous observation that ICAM-1 could costimulate T cell proliferation without detectable IL-2 or IL-4 production (Boussiotis, V., et al *J. Exp. Med.* (accepted for publication)). These data indicate that the BB-1 monoclonal antibody recognizes an epitope on the B7-1 protein and that this epitope is also found on a distinct B7-3 protein, which also has costimulatory function. Phenotypic and blocking studies demonstrate that the BB-1 monoclonal antibody could detect one (on B7 negative cells) or both (on B7 positive cells) of these proteins. In contrast, the anti-B7 monoclonal antibodies, 133 and B1.1 detect only the B7-1 protein. Taken together, these results suggest that by 48 hours post B-cell activation by crosslinking of surface immunoglobulin or MHC class II, B cells express two distinct CTLA4 binding counter-receptors, one identified by both anti-B7 and BB-1 monclonal antibodies and the other identified only by BB-1 monoclonal antibody.

The B7-2 antigen is not detectable on activated B cells after 12 hours, but by 24 hours it is strongly expressed and functional. This molecule appears to signal via CD28 since proliferation and IL-2 production are completely blocked by Fab anti-CD28 monoclonal antibody. The B7-2 antigen appears to be lost by 48 hours post-activation, a time when activated B cells strongly express both B7-1 and B7-3. At 48 hours post activation, all IL-2 secretion seems to be accounted for by B7-1 costimulation, since anti-B7 monoclonal antibody completely inhibits IL-2 production.

Previous studies and results presented here demonstrate that B7 (B7-1) is neither expressed (Freedman, A. S. et al. (1987) *Immunol.* 137, 3260–3267; Freedman, A. S., et al. (1991) *Cell. Immunol.* 137, 429–437) nor capable of costimulating T cell proliferation or IL-2 secretion until 48 hours post B-cell activation. Previous studies have shown that activation of T cells via the TCR in the absence of costimulation (Gimmi, C. D., et al. (1993) *Proc. Natl. Acad. Sci USA* 90: 6586–6590, Schwartz, R. H., et al. (1989) *Cold Spring Harb. Symp. Quant. Biol* 54, 605–10; Beverly, B., et al. (1992) *Int. Immunol.* 4, 661–671.) and lack of IL-2 (Boussiotis, V., et al *J. Exp. Med.* (submitted); Beverly, B., et al. (1992) *Int. Immunol.* 4, 661–671; Wood, M., et al. (1993) *J. Exp. Med.* 177, 597–603) results in anergy. If B7-1 were the only costimulatory molecule capable of inducing IL-2 secretion, T cells would be anergized within the first 24 hours following activation since there is no B7-1 present to costimulate IL-2 production. Therefore, the existence of another, early inducible costimulatory molecule, which can costimulate IL,-2 secretion during the first 24 hours would be necessary to induce an effective immune response rather than anergy. The appearance of the early CTLA4 binding counter-receptor, B7-2, between 12 and 24 hours post B cell activation, fulfills this function.

Two observations shed light on the biologic and potential clinical significance of these two additional CTLA4 binding counter-receptors. First, Gordon Freeman (Dana Farber Cancer Institute) and Arlene Sharpe (Brigham and Women's Hospital) have recently developed a B7 (B7-1) deficient mouse and its antigen presenting cells can still bind CTLA4-Ig (manuscript in preparation). This mouse is viable and isolated mononuclear cells produce detectable levels of IL-2 in vitro. Therefore, an alternative CD28 costimulatory counter-receptor or an alternative IL-2 producing pathway must be functional. Second, thus far the most effective reagents to induce antigen specific anergy in murine and human systems are CTLA4-Ig and Fab anti-CD28, whereas anti-B7 monoclonal antibodies have been much less effective (Harding, F. A., et al. (1992) *Nature.* 356, 607–609; Lenschow, D. J., et al. (1992) *Science.* 257, 789–792; Chen, L., et al. (1992) *Cell.* 71, 1093–1102; Tan, P., et al. (1993) *J. Exp. Med.* 177, 165–173.). These observations are also consistent with the hypothesis that alternative CTLA4/CD28 ligands capable of inducing IL-2 exist, and taken together with our present results, suggest that all three CTLA4 binding counter-receptors may be critical for the induction of T cell immunity. Furthermore, their blockade will likely be required for the induction of T cell anergy. Therefore, the identification and characterization of these molecules will be critical to our understanding of the induction of the immune response as well as for the generation of antigen specific tolerance.

Identical results have been observed in the murine system with the identification of two CTLA4 binding ligands, corresponding to the human B7-1 and B7-2 molecules. APCs in the B7 deficient mouse bind to the CTLA4 and can induce IL-2 secretion. Taken together, these observations indicate that multiple CTLA-4 binding counter-receptors exist and sequentially costimulate T cell activation in the murine system.

Example 4: Cloning, Sequencing and Expression of the B7-2 Activation Antigen

A. Construction of cDNA Library

A cDNA library was constructed in the pCDM8 vector (Seed, *Nature,* 329: 840 (1987)) using poly (A)$^+$ RNA from the human anti-IgM activated B cells as described (Aruffo et al, *Proc. Natl. Acad. Sci. USA,* 84: 3365 (1987)).

Splenic B cells were cultured at $2 \times 10^6$ cells/ml in complete culture media, {RPMI 1640 with 10% heat inactivated fetal calf serum (FCS), 2 mM glutamine, 1 mM sodium pyruvate, penicillin (100 units/ml), streptomycin sulfate (100 $\mu$g/ml) and gentamycin sulfate (5 $\mu$g/ml)}, in tissue culture flasks and were activated by crosslinking of sIg with affinity purified rabbit anti-human IgM coupled to Affi-Gel 702 beads (Bio-Rad), Richmond, Calif.) (Boyd, A. W., et al., (1985) *J. Immunol.* 134,1516). Activated B cells were harvested after ⅙, ½, 4, 8 12, 24, 48, 72 and 96 hours.

RNA was prepared by homogenizing activated B cells in a solution of 4M guanidine thiocyanate, 0.5% sarkosyl, 25 mM EDTA, pH 7.5, 0.13% Sigma anti-foam A, and 0.7% mercaptoethanol. RNA was purified from the homogenate by centrifugation for 24 hour at 32,000 rpm through a solution of 5.7M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)$^+$ RNA used in cDNA library construction was purified by two cycles of oligo (dT)-cellulose selection.

Complementary DNA was synthesized from 5.5 $\mu$g of anti-IgM activated human B cell poly(A)$^+$ RNA in a reaction containing 50 mM Tris, pH 8.3, 75 mM KCl, 3 mM MgCl$_2$, 10 mM dithiothreitol, 500 $\mu$M dATP, dCTP, dGTP, dTTP, 50 $\mu$g/ml oligo(dT)$_{12-18}$, 180 units/ml RNasin, and 10,000 units/ml Moloney-MLV reverse transcriptase in a total volume of 55$\mu$l at 37° for 1 hr. Following reverse transcription, the cDNA was converted to double-stranded DNA by adjusting the solution to 25 mM Tris, pH 8.3, 100 mM KCl, 5 mM MgCl$_2$, 250 $\mu$M each dATP, dCTP, dGTP, dTTP, 5 mM dithiothreitol, 250 units/ml DNA polymerase I, 8.5 units/ml ribonuclease H and incubating at 16° for 2 hr. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier. In addition, cDNA was synthesized from 4 μg of anti-IgM activated human B cell poly(A)+ RNA in a reaction containing 50 mM Tris, pH 8.8, 50 μg/ml oligo(dT)$_{12-18}$, 327 units/ml RNasin, and 952 units/ml AMV reverse transcriptase in a total volume of 100 μl at 42° for 0.67 hr. Following reverse transcription, the reverse transcriptase was inactivated by heating at 70° for 10 min. The cDNA was converted to double-stranded DNA by adding 320 μl H$_2$O and 80 μl of a solution of 0.1M Tris, pH 7.5, 25 mM MgCl$_2$, 0.5M KCl, 250 g/ml bovine serum albumin, and 50 mM dithiothreitol, and adjusting the solution to 200 μM each dATP, dCTP, dGTP, dTTP, 50 units/ml DNA polymerase I, 8 units/ml ribonuclease H and incubating at 160 for 1 hour and 220 for 1 hour. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier.

The DNA from 4 μg of AMV reverse transcription and 2 μg of Moloney MLV reverse transcription was combined. Non-selfcomplementary BstXI adaptors were added to the DNA as follows: The double-stranded cDNA from 6 μg of poly(A)+ RNA was incubated with 3.6 μg of a kinased oligonucleotide of the sequence CTTTAGAGCACA (SEQ ID NO: 15) and 2.4 μg of a kinased oligonucleotide of the sequence CTCTAAAG (SEQ ID NO: 16) in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 0.45 ml at 150 for 16 hours. EDTA was added to 34 mM and the solution was extracted with an equal volume of 50% phenol, 49% chloroform, 1% isoamyl alcohol. DNA was precipitated with two volumes of ethanol in the presence of 2.5M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) was pooled and ethanol precipitated.

The pCDM8 vector was prepared for cDNA cloning by digestion with BstXI and purification on an agarose gel. Adaptored DNA from 6 μg of poly(A)+ RNA was ligated to 2.25 μg of BstXI cut pCDM8 in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 1.5 ml at 15° for 24 hr. The ligation reaction mixture was transformed into competent *E.coli* MC1061/P3 and a total of 4,290,000 independent cDNA clones were obtained.

Plasmid DNA was prepared from a 500 ml culture of the original transformation of the cDNA library. Plasmid DNA was purified by the alkaline lysis procedure followed by twice banding in CsCl equilibrium gradients (Maniatis et al, *Molecular Cloning: A Laboratory Manual*, Cold Spring Harbor, N.Y. (1987)).

B. Cloning Procedure

In the first round of screening, thirty 100 mm dishes of 50% confluent COS cells were transfected with 0.05 μg/ml anti-IgM activated human B cells library DNA using the DEAE-Dextran method (Seed et al, *Proc. Natl. Acad. Sci. USA*, 84: 3365 (1987)). The cells were trypsinized and re-plated after 24 hours. After 47 hours, the cells were detached by incubation in PBS/0.5 mM EDTA, pH 7.4/ 0.02% Na azide at 37° C. for 30 min. The detached cells were treated with 10 μg/ml/CTLA4Ig and CD28Ig for 45 minutes at 4° C. Cells were washed and distributed into panning dishes coated with affinity-purified Goat anti-human IgG antibody and allowed to attach at room temperature. After 3 hours, the plates were gently washed twice with PBS/0.5 mM EDTA, pH 7.4/0.02% Na azide, 5% FCS and once with 0.15M NaCl, 0.01 M Hepes, pH 7.4, 5% FCS. Episomal DNA was recovered from the panned cells and transformed into *E. coli* DH10B/P3. The plasmid DNA was re-introduced into COS cells via spheroplast fusion as described (Seed et al, *Proc. Natl. Acad Sci. USA*, 84: 3365 (1987)) and the cycle of expression and panning was repeated twice. In the second and third rounds of selection, after 47 hours, the detached COS cells were first incubated with α-B7-1 mAbs (133 and B1.1, 10 μg/ml), and COS cells expressing B7.1 were removed. α-mouse IgG and IgM coated magnetic beads were used to select COS cells as in round 1. After the third round, plasmid DNA was prepared from individual colonies and transfected into COS cells by the DEAE-Dextran method. Expression of B7-2 on transfected COS cells was analyzed by indirect immunofluorescence with CTLA4Ig.

After the final round of selection, plasmid DNA was prepared from individual colonies. A total of 14 of 48 candidate clones contained a cDNA insert of 1.2 kb. Plasmid DNA from one of these clones was transfected into COS cells. This clone was strongly positive for B7-2 expression by indirect immunofluorescence using CTLA4-Ig and flow cytometric analysis.

C. Sequencing

The B7-2 cDNA insert in clone #29 was sequenced in the pCDM8 expression vector employing the following strategy. Initial sequencing was performed using sequencing primers T7, CDM8R (Invitrogen) homologous to pCDM8 vector sequences adjacent to the cloned B7-2 cDNA (see FIG. 13). Sequencing was performed using dye terminal, ABI automated DNA sequencer. (ABI, Foster City, Calif.). DNA sequencing using these primers was used to design additional sequencing primers (see FIG. 13). This cycle of sequencing and selection of additional primers was continued until the B72 cDNA was completely sequenced on both strands.

The clone contained an insert of 1.2 kilobases (kb) with a single long open reading frame of 987 nucleotides and approximately 27 nucleotides of 3' noncoding sequences (FIG. 8). The predicted amino acid sequence encoded by the open reading frame of the protein is shown below the nucleotide sequence in FIG. 8 (see SEQ ID NO: 1). The encoded protein, B7-2, is predicted to be 329 amino acids in length (SEQ ID NO: 2). This protein sequence exhibits many features common to other type 1 Ig superfamily membrane proteins. Protein translation probably begins at the ATG codon (nucleotide 107) because this DNA sequence in this region shows features often found at eukaryotic translation initiation sites (Kozak, M. (1987) *Nucl. Acids Res.* 15: 8125–8148). The hydrophobic sequence at the amino terminus of the B7-2 protein (amino acids 1 to 23) has the characteristics of a secretory signal peptide; the method of von Heigne (*Nucl. Acids Res.* 14: 4683) predicts cleavage between the alanines at positions 23 and 24. Processing at this site would result in an unmodified B7-2 membrane bound protein of 306 amino acid having a molecular weight of approximately 36 kDa. This protein would consist of an approximately 220 amino acid extracellular Ig superfamily V and C like domains, a hydrophobic transmembrane domain of about 20 amino acids and a long cytoplasmic domain of approximately 60 amino acids. The homologies to the Ig superfamily are due to the two contiguous Ig-like domains in the extracellular region bound by the cysteines at positions 40 to 110 and 157 to 218. The extracellular domain also contains eight potential N-linked glycosylation sites. Comparison of both the nucleotide and protein sequences of B7-2 with the GenBank and EMBL databases yielded significant homology (~25%) with both human B7-1 and murine B7.

FIG. 14 represents the comparison of the amino acid sequences for human B7-2 (hB7-2) (SEQ ID NO: 2), human B7-1 (hB7-1) (SEQ ID NO: 22 and 23) and murine B7 (mB7) (SEQ ID NO: 24 and 25). Vertical lines show identical amino acids between the hB7-2 and hB7-1 or hB7-1 and mB7. Identical amino acids between hB7-2 and mB7 are not shown. The hB7-2 protein exhibits the same general structure as hB7-1 as defined by the common cysteines which limit the Ig superfamily domains and by many other common amino acids. Since both hB7-1 and mB7 have been shown to bind to both human and murine CTLA4 and human and murine CD28 the amino acids in common between these B7 proteins will be those necessary to comprise a CTLA4 or CD28 binding sequence. An example of such a sequence would be the KYMGRTSFD (SEQ ID NO: 17) (position 81–89, hB7-2) or KSQDNVTE-LYDVS (SEQ ID NO: 18) (position 188–200, hB7-2). The B7 sequences share a highly positive charged domain with the cytoplasmic portion WKWKKKKRPRNSYKC (SEQ ID NO: 19) (position 269–282, hB7-2) which is probably involved in intracellular signaling.

Example 5: Characterization of the Recombinant B7-2 Activation Antigen

A. Immunofluorescence

Figure 9:
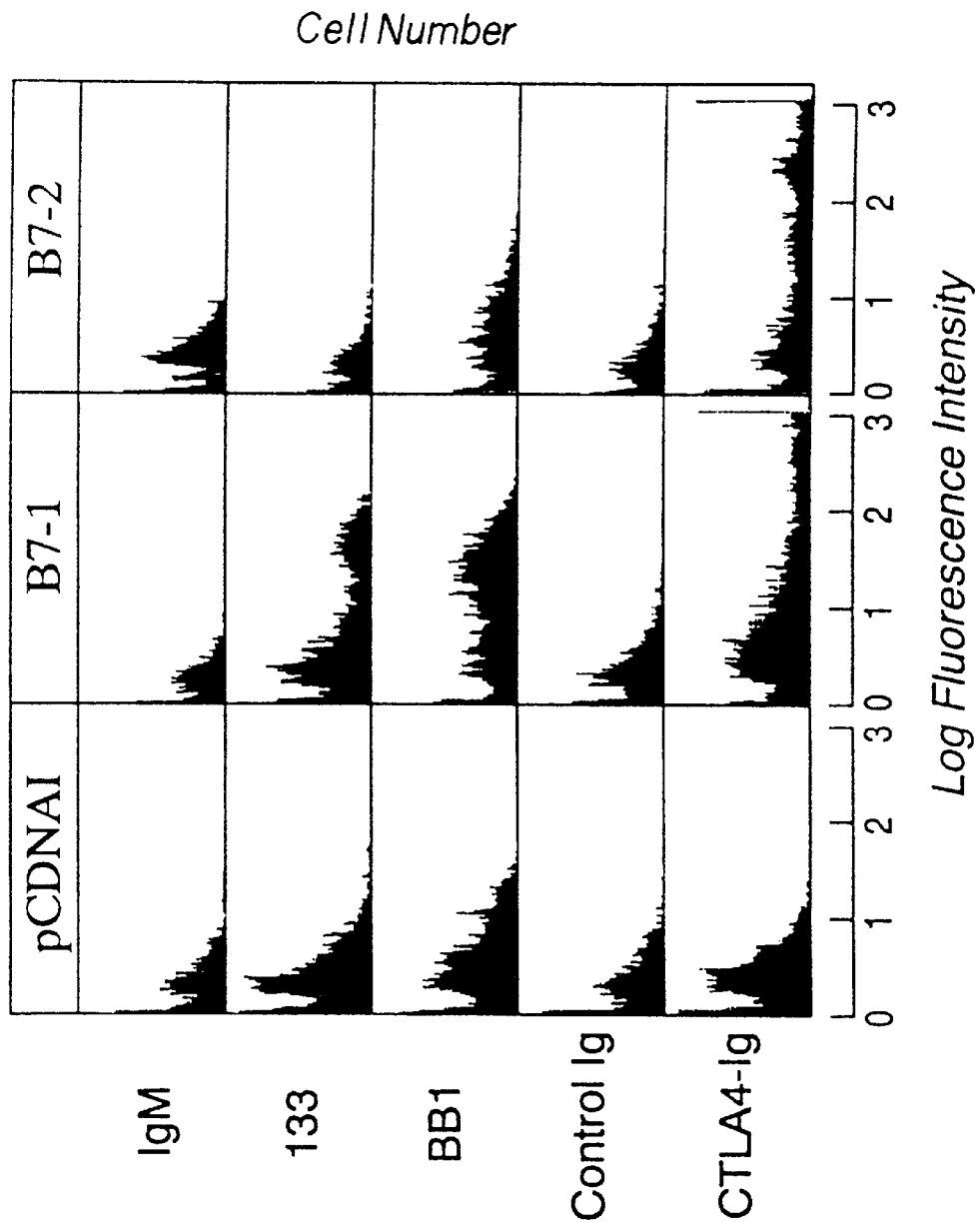
FIG. 9 is a graphic representation of the staining of COS cells transfected with control plasmid (pCDNAI), plasmid expressing B7-1 (B7-1), or plasmid expressing B7-2 (B7-2) as measured by flow cytometry. The transfected cells were stained with either control mAb (IgM), anti-B7 mAbs 133 and BB-1, recombinant protein CTLA4Ig, or isotype matched control Ig protein followed by the appropriate second FITC labelled immunoglobulin. MAbs 133, BB-1, and protein CTLA4Ig stain the B7-1 expressing cells whereas only CTLA4Ig stains the B7-2 expressing cells.

COS cells transfected with either vector DNA (pCDNAI), or an expression plasmid containing B7-1 (B7-1) or B7-2 (B7-2) were prepared. After 72 hours, the transfected COS cells were detached by incubation in PBS containing 0.5 mM EDTA and 0.02% Na azide for 30 min. at 37° C. Cells were analyzed for cell surface expression by indirect immunofluorescence and flow cytometry (FIG. 9). Cell surface expression of B7-1 ws detected with mAbs 133 and BB-1 and with CTLA4Ig whereas B7-2 reacted only with CTLA4Ig. Neither of the B7 transfectants showed any staining with the isotype controls (IgM or control Ig). The vector transfected COS cells showed no staining with any of the detection reagents. In addition, none of the cells showed any staining with the FITC labeled detection reagents.

B. Costimulation

Figure 10:
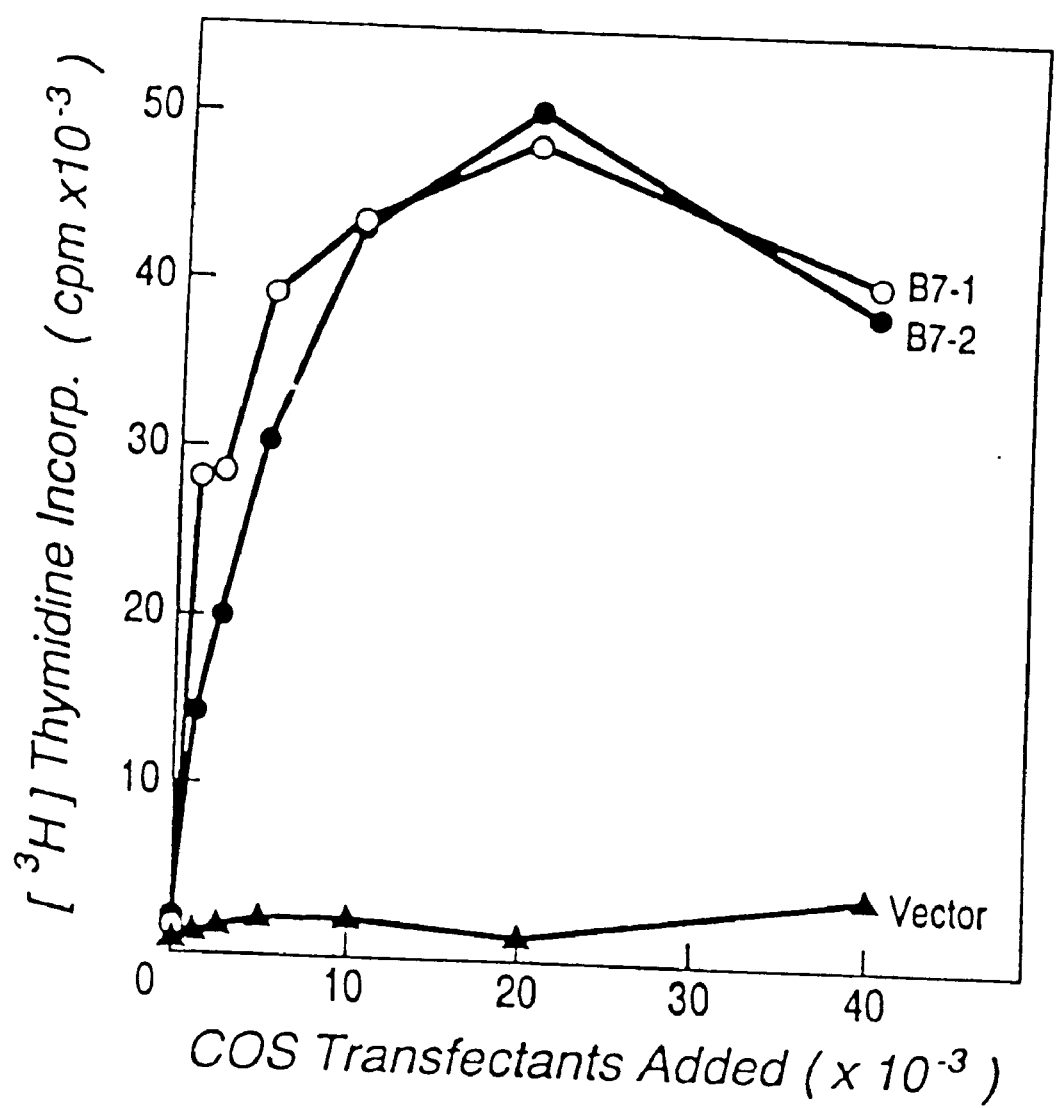
FIG. 10 is a graphic representation of the proliferation of CD28+T cells submitogenically stimulated with phorbol myristic acid (PMA)by COS cells transfected with vector alone or vectors directing the expression of either B7-1 or B7-2. Both B7-1 and B7-2 expressing COS cells provide costimulatory signals to the PMA stimulated T cells in a dose dependent fashion.

COS cells transfected with vector alone or with plasmids expressing B7-1 or B7-2 were mixed with CD4+ T cells stimulated with submitogenic amounts of PMA. both B7-1 and B7-2 expressing COS cells induce the proliferation of CD4+ T cells (FIG. 10) in a dose dependent fashion. Vector transfected cells showed no stimulation of proliferation.

C. Inhibition of B7-1 and B7-2 Induced Costimulation

Figures 11A, 11B, 11C, 11D:
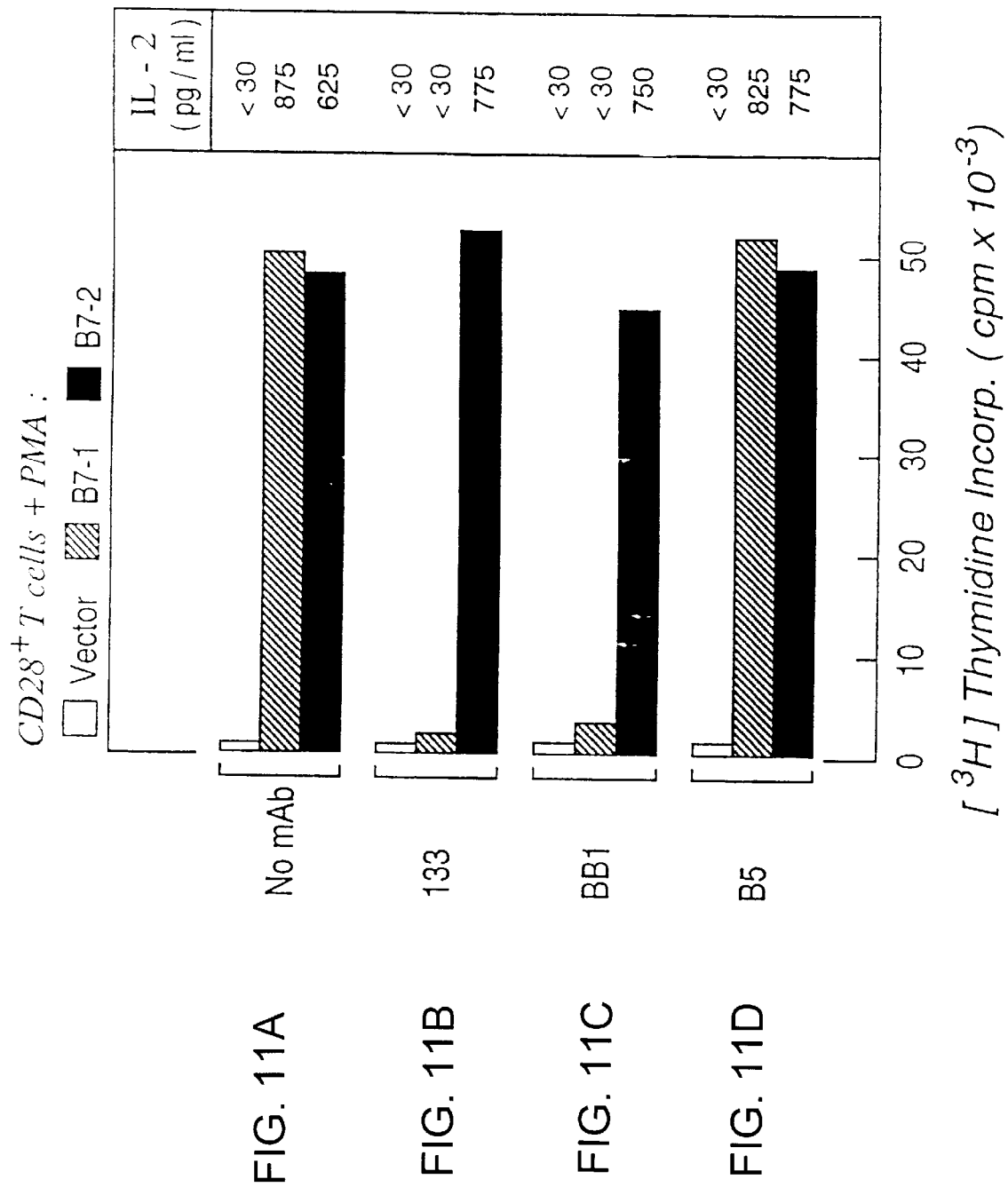
FIG. 11 is a graphic representation of the inhibition by mAbs and recombinant proteins of the proliferation of CD28+T cells stimulated by PMA and COS cells transfected with vector alone (vector), or with a vector expressing B7-1 (B7-1) or B7-2 (B7-2). Inhibition studies were performed with the addition of either no antibody (no mAb)(panel A), anti-B7 mAb 133 (133) (panel B), anti-B7 mAb BB-1 (BB1)(panel C), anti-B5 mAb (B5)(panel D), Fab fragment of anti-CD28 (CD28 Fab)(panel E), CTLA4Ig (CTLA4-Ig) (panel F), or Ig control protein (control Ig) (panel G) to the PMA stimulated COS cell admixed CD28+T cells. MAbs 133, BB-1, CD28 Fab, and protein CTLA4Ig all inhibit the COS expressed B7-1 proliferation of T cells whereas only CTLA4Ig inhibits the COS expressed B7-2 proliferation.

The blocking of stimulation of CD4+ T cells by B7-1 and B7-2 transfected COS cells was tested by adding mAbs (133, BB-1, B5, CD28 Fab) and recombinant proteins (CTLA4Ig, control Ig) to mixtures of T cells and transfected cells. Costimulation by B7-1 expressing COS cells was inhibited by mAbs 133, CD28 Fab and BB-1 and by CTLA4Ig (FIG. 11) whereas B7-2 expressing COS cells were inhibited by CTLA4Ig and CD28 Fab only. Costimulaton by both B7-1 and B7-2 was resistant to the effects of control mAb B7 and control Ig protein.

D. IL-2 production

Costimulation of CD4+ T cells by PMA and COS cells expressing B7-1 or B7-2 led to the production of interleukin-2 (FIG. 12) MAbs and recombinant proteins which inhibited T cell proliferation (FIG. 11) also eliminate the production of IL-2 (FIG. 12).

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid which encodes B7-2 antigen consisting of the nucleotide sequence shown in FIG. 8, SEQ ID NO: 1.

2. An isolated nucleic acid which encodes B7-2 antigen consisting of the coding region of the nucleotide sequence shown in FIG. 8, SEQ ID NO: 1.

3. An isolated nucleic acid which encodes B7-2 antigen consisting of a nucleotide sequence which differs from the nucleotide sequence shown in FIG. 8, SEQ ID NO: 1, due to degeneracy in the genetic code.

4. An isolated nucleic acid which encodes B7-2 antigen consisting of a nucleotide sequence which differs from the coding region of the nucleotide sequence shown in FIG. 8, SEQ ID NO: 1, due to degeneracy in the genetic code.

5. An isolated nucleic acid consisting of a nucleotide sequence which encodes the extracellular domain of the B7-2 amino acid sequence shown in FIG. 8, SEQ ID NO: 2.

6. An isolated nucleic acid consisting of a nucleotide sequence which encodes amino acid residues 24–245 of the B7-2 amino acid sequence shown in FIG. 8, SEQ ID NO: 2.

7. An isolated B7-2 protein consisting of the amino acid sequence shown in FIG. 8, SEQ ID NO: 2.

8. An isolated B7-2 protein consisting of amino acid residues 24–329 of the amino acid sequence shown in FIG. 8, SEQ ID NO: 2.

9. A soluble B7-2 protein consisting of the extracellular domain of the amino acid sequence shown in FIG. 8, SEQ ID NO: 2.

* * * * *

UNITED STATES PATENT AND TRADEMARK OFFICE
CERTIFICATE OF CORRECTION

PATENT NO. : 5,942,607
APPLICATION NO. : 08/101624
DATED : August 24, 1999
INVENTOR(S) : Freeman et al.

It is certified that error appears in the above-identified patent and that said Letters Patent is hereby corrected as shown below:

On the title page, item:
    [73] please replace:
"Assignee: Dana-Farber Cancer Institute, Boston, MA" with
--Assignees: Dana-Farber Cancer Institute, Boston, MA; Genetics Institute, LLC, Cambridge, MA--

Signed and Sealed this

Fifteenth Day of August, 2006

JON W. DUDAS
*Director of the United States Patent and Trademark Office*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 1120 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 107..1093

(xi) SEQUENCE DESCRIPTION: SEQ ID NO:1:

```
CACAGGGTGA AAGCTTTGCT TCTCTGCTGC TGTAACAGGG ACTAGCACAG ACACACGGAT         60

GAGTGGGGTC ATTTCCAGAT ATTAGGTCAC AGCAGAAGCA GCCAAA ATG GAT CCC          115
                                                 Met Asp Pro
                                                  1
```

```
CAG TGC ACT ATG GGA CTG AGT AAC ATT CTC TTT GTG ATG GCC TTC CTG        163
Gln Cys Thr Met Gly Leu Ser Asn Ile Leu Phe Val Met Ala Phe Leu
          5                  10                  15

CTC TCT GGT GCT GCT CCT CTG AAG ATT CAA GCT TAT TTC AAT GAG ACT        211
Leu Ser Gly Ala Ala Pro Leu Lys Ile Gln Ala Tyr Phe Asn Glu Thr
 20                  25                  30                  35

GCA GAC CTG CCA TGC CAA TTT GCA AAC TCT CAA AAC CAA AGC CTG AGT        259
Ala Asp Leu Pro Cys Gln Phe Ala Asn Ser Gln Asn Gln Ser Leu Ser
                 40                  45                  50

GAG CTA GTA GTA TTT TGG CAG GAC CAG GAA AAC TTG GTT CTG AAT GAG        307
Glu Leu Val Val Phe Trp Gln Asp Gln Glu Asn Leu Val Leu Asn Glu
             55                  60                  65

GTA TAC TTA GGC AAA GAG AAA TTT GAC AGT GTT CAT TCC AAG TAT ATG        355
Val Tyr Leu Gly Lys Glu Lys Phe Asp Ser Val His Ser Lys Tyr Met
         70                  75                  80

GGC CGC ACA AGT TTT GAT TCG GAC AGT TGG ACC CTG AGA CTT CAC AAT        403
Gly Arg Thr Ser Phe Asp Ser Asp Ser Trp Thr Leu Arg Leu His Asn
     85                  90                  95

CTT CAG ATC AAG GAC AAG GGC TTG TAT CAA TGT ATC ATC CAT CAC AAA        451
Leu Gln Ile Lys Asp Lys Gly Leu Tyr Gln Cys Ile Ile His His Lys
100                 105                 110                 115

AAG CCC ACA GGA ATG ATT CGC ATC CAC CAG ATG AAT TCT GAA CTG TCA        499
Lys Pro Thr Gly Met Ile Arg Ile His Gln Met Asn Ser Glu Leu Ser
                120                 125                 130

GTG CTT GCT AAC TTC AGT CAA CCT GAA ATA GTA CCA ATT TCT AAT ATA        547
Val Leu Ala Asn Phe Ser Gln Pro Glu Ile Val Pro Ile Ser Asn Ile
            135                 140                 145

ACA GAA AAT GTG TAC ATA AAT TTG ACC TGC TCA TCT ATA CAC GGT TAC        595
Thr Glu Asn Val Tyr Ile Asn Leu Thr Cys Ser Ser Ile His Gly Tyr
        150                 155                 160

CCA GAA CCT AAG AAG ATG AGT GTT TTG CTA AGA ACC AAG AAT TCA ACT        643
Pro Glu Pro Lys Lys Met Ser Val Leu Leu Arg Thr Lys Asn Ser Thr
165                 170                 175

ATC GAG TAT GAT GGT ATT ATG CAG AAA TCT CAA GAT AAT GTC ACA GAA        691
Ile Glu Tyr Asp Gly Ile Met Gln Lys Ser Gln Asp Asn Val Thr Glu
180                 185                 190                 195

CTG TAC GAC GTT TCC ATC AGC TTG TCT GTT TCA TTC CCT GAT GTT ACG        739
Leu Tyr Asp Val Ser Ile Ser Leu Ser Val Ser Phe Pro Asp Val Thr
                200                 205                 210

AGC AAT ATG ACC ATC TTC TGT ATT CTG GAA ACT GAC AAG ACG CGG CTT        787
Ser Asn Met Thr Ile Phe Cys Ile Leu Glu Thr Asp Lys Thr Arg Leu
            215                 220                 225

TTA TCT TCA CCT TTC TCT ATA GAG CTT GAG GAC CCT CAG CCT CCC CCA        835
Leu Ser Ser Pro Phe Ser Ile Glu Leu Glu Asp Pro Gln Pro Pro Pro
        230                 235                 240

GAC CAC ATT CCT TGG ATT ACA GCT GTA CTT CCA ACA GTT ATT ATA TGT        883
Asp His Ile Pro Trp Ile Thr Ala Val Leu Pro Thr Val Ile Ile Cys
245                 250                 255

GTG ATG GTT TTC TGT CTA ATT CTA TGG AAA TGG AAG AAG AAG CGG            931
Val Met Val Phe Cys Leu Ile Leu Trp Lys Trp Lys Lys Lys Arg
260                 265                 270                 275

CCT CGC AAC TCT TAT AAA TGT GGA ACC AAC ACA ATG GAG AGG GAA GAG        979
Pro Arg Asn Ser Tyr Lys Cys Gly Thr Asn Thr Met Glu Arg Glu Glu
                280                 285                 290

AGT GAA CAG ACC AAG AAA AGA GAA AAA ATC CAT ATA CCT GAA AGA TCT       1027
Ser Glu Gln Thr Lys Lys Arg Glu Lys Ile His Ile Pro Glu Arg Ser
            295                 300                 305

GAT GAA GCC CAG CGT GTT TTT AAA AGT TCG AAG ACA TCT TCA TGC GAC       1075
Asp Glu Ala Gln Arg Val Phe Lys Ser Ser Lys Thr Ser Ser Cys Asp
        310                 315                 320
```

```
AAA AGT GAT ACA TGT TTT TAATTAAAGA GTAAAGCCCA AAAAAAA          1120
Lys Ser Asp Thr Cys Phe
    325
```

(2) INFORMATION FOR SEQ ID NO:2:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Pro Gln Cys Thr Met Gly Leu Ser Asn Ile Leu Phe Val Met
 1               5                  10                  15

Ala Phe Leu Leu Ser Gly Ala Ala Pro Leu Lys Ile Gln Ala Tyr Phe
                20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
        50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:3:

TAATACGACT CACTATAGGG                                         20

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:4:

TAAGGTTCCT TCACAAAG                                           18

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

ACTGGTAGGT ATGGAAGATC C                                     21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

ATGCGAATCA TTCCTGTGGG C                                     21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

AAAGCCCACA GGAATGATTC G                                     21

(2) INFORMATION FOR SEQ ID NO:8:

(i) SEQUENCE CHARACTERISTICS:
        (A) LENGTH: 21 base pairs (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:8:

CTCTCAAAAC CAAAGCCTGA G                                              21

(2) INFORMATION FOR SEQ ID NO:9:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:9:

TTAGGTCACA GCAGAAGCAG C                                              21

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:10:

TCTGGAAACT GACAAGACGC G                                              21

(2) INFORMATION FOR SEQ ID NO:11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:11:

CTCAGGCTTT GGTTTTGAGA G                                              21

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:12:

CACTCTCTTC CCTCTCCATT G                                              21

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide -continued (xi) SEQUENCE DESCRIPTION: SEQ ID NO:13:

GACAAGCTGA TGGAAACGTC G                                              21

(2) INFORMATION FOR SEQ ID NO:14:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:14:

CAATGGAGAG GGAAGAGAGT G                                              21

(2) INFORMATION FOR SEQ ID NO:15:

(i) SEQUENCE CHARACTERISTICS:
       (A) LENGTH: 12 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:15:

CTTTAGAGCA CA                                                        12

(2) INFORMATION FOR SEQ ID NO:16:

(i) SEQUENCE CHARACTERISTICS:
       (A) LENGTH: 8 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:16:

CTCTAAAG                                                             8

(2) INFORMATION FOR SEQ ID NO:17:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (xi) SEQUENCE DESCRIPTION: SEQ ID NO:17:

Lys Tyr Met Gly Arg Thr Ser Phe Asp
                  5

(2) INFORMATION FOR SEQ ID NO:18:

(i) SEQUENCE CHARACTERISTICS:
       (A) LENGTH: 13 amino acids
       (B) TYPE: amino acid
       (D) TOPOLOGY: linear (ii) MOLECULE TYPE: peptide (xi) SEQUENCE DESCRIPTION: SEQ ID NO:18:

Lys Ser Gln Asp Asn Val Thr Glu Lys Tyr Asp Val Ser
              5                  10

(2) INFORMATION FOR SEQ ID NO:19:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:19:

Trp Lys Trp Lys Lys Lys Arg Pro Arg Asn Ser Tyr Lys Cys
                5                    10                   15

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:20:

TGGCCCATGG CTTCAGA                                                      17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:21:

GCCAAAATGG ATCCCCA                                                      17

(2) INFORMATION FOR SEQ ID NO:22:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Homo sapien
        (F) TISSUE TYPE: lymphoid
        (G) CELL TYPE: B cell
        (H) CELL LINE: Raji (vii) IMMEDIATE SOURCE:
        (A) LIBRARY: cDNA in pCDM8 vector
        (B) CLONE: B7, Raji clone #13

(viii) POSITION IN GENOME:
        (A) CHROMOSOME/SEGMENT: 3

(ix) FEATURE:
        (A) NAME/KEY: Open reading frame (translated region)
        (B) LOCATION: 318 to 1181 bp
        (C) IDENTIFICATION METHOD: similarity to other pattern (ix) FEATURE:
        (A) NAME/KEY: Alternate polyadenylation signal (B) LOCATION: 1474 to 1479 bp
            (C) IDENTIFICATION METHOD: similarity to other pattern (x) PUBLICATION INFORMATION:
        (A) AUTHORS: FREEMAN, GORDON J.
                     FREEDMAN, ARNOLD S.
                     SEGIL, JEFFREY M.
                     LEE, GRACE
                     WHITMAN, JAMES F.
                     NADLER, LEE M.
        (B) TITLE: B7, A New Member Of The Ig Superfamily With
                   Unique Expression On Activated And Neoplastic B Cells
        (C) JOURNAL: The Journal of Immunology
        (D) VOLUME: 143
        (E) ISSUE: 8
        (F) PAGES: 2714-2722
        (G) DATE: 15-OCT-1989
        (H) RELEVANT RESIDUES IN SEQ ID NO:22: FROM 1 TO 1491

(xi) SEQUENCE DESCRIPTION: SEQ ID NO:22:

```
CCAAAGAAAA AGTGATTTGT CATTGCTTTA TAGACTGTAA GAAGAGAACA TCTCAGAAGT        60

GGAGTCTTAC CCTGAAATCA AAGGATTTAA AGAAAAAGTG GAATTTTTCT TCAGCAAGCT       120

GTGAAACTAA ATCCACAACC TTTGGAGACC CAGGAACACC CTCCAATCTC TGTGTGTTTT       180

GTAAACATCA CTGGAGGGTC TTCTACGTGA GCAATTGGAT TGTCATCAGC CCTGCCTGTT       240

TTGCACCTGG GAAGTGCCCT GGTCTTACTT GGGTCCAAAT TGTTGGCTTT CACTTTTGAC       300

CCTAAGCATC TGAAGCC ATG GGC CAC ACA CGG AGG CAG GGA ACA TCA CCA TCC      353
                   Met Gly His Thr Arg Arg Gln Gly Thr Ser Pro Ser
                           -30                 -25

AAG TGT CCA TAC CTG AAT TTC TTT CAG CTC TTG GTG CTG GCT GGT CTT        401
Lys Cys Pro Tyr Leu Asn Phe Phe Gln Leu Leu Val Leu Ala Gly Leu
        -20                 -15                 -10

TCT CAC TTC TGT TCA GGT GTT ATC CAC GTG ACC AAG GAA GTG AAA GAA        449
Ser His Phe Cys Ser Gly Val Ile His Val Thr Lys Glu Val Lys Glu
    -5                   1                   5                  10

GTG GCA ACG CTG TCC TGT GGT CAC AAT GTT TCT GTT GAA GAG CTG GCA        497
Val Ala Thr Leu Ser Cys Gly His Asn Val Ser Val Glu Glu Leu Ala
                15                  20                  25

CAA ACT CGC ATC TAC TGG CAA AAG GAG AAG AAA ATG GTG CTG ACT ATG        545
Gln Thr Arg Ile Tyr Trp Gln Lys Glu Lys Lys Met Val Leu Thr Met
            30                  35                  40

ATG TCT GGG GAC ATG AAT ATA TGG CCC GAG TAC AAG AAC CGG ACC ATC        593
Met Ser Gly Asp Met Asn Ile Trp Pro Glu Tyr Lys Asn Arg Thr Ile
        45                  50                  55

TTT GAT ATC ACT AAT AAC CTC TCC ATT GTG ATC CTG GCT CTG CGC CCA        641
Phe Asp Ile Thr Asn Asn Leu Ser Ile Val Ile Leu Ala Leu Arg Pro
60                  65                  70

TCT GAC GAG GGC ACA TAC GAG TGT GTT GTT CTG AAG TAT GAA AAA GAC        689
Ser Asp Glu Gly Thr Tyr Glu Cys Val Val Leu Lys Tyr Glu Lys Asp
75                  80                  85                  90

GCT TTC AAG CGG GAA CAC CTG GCT GAA GTG ACG TTA TCA GTC AAA GCT        737
Ala Phe Lys Arg Glu His Leu Ala Glu Val Thr Leu Ser Val Lys Ala
                95                 100                 105

GAC TTC CCT ACA CCT AGT ATA TCT GAC TTT GAA ATT CCA ACT TCT AAT        785
Asp Phe Pro Thr Pro Ser Ile Ser Asp Phe Glu Ile Pro Thr Ser Asn
            110                 115                 120

ATT AGA AGG ATA ATT TGC TCA ACC TCT GGA GGT TTT CCA GAG CCT CAC        833
Ile Arg Arg Ile Ile Cys Ser Thr Ser Gly Gly Phe Pro Glu Pro His
        125                 130                 135

CTC TCC TGG TTG GAA AAT GGA GAA GAA TTA AAT GCC ATC AAC ACA ACA        881
Leu Ser Trp Leu Glu Asn Gly Glu Glu Leu Asn Ala Ile Asn Thr Thr
    140                 145                 150

GTT TCC CAA GAT CCT GAA ACT GAG CTC TAT GCT GTT AGC AGC AAA CTG        929
```

```
Val Ser Gln Asp Pro Glu Thr Glu Leu Tyr Ala Val Ser Ser Lys Leu
155                 160                 165                 170

GAT TTC AAT ATG ACA ACC AAC CAC AGC TTC ATG TGT CTC ATC AAG TAT          977
Asp Phe Asn Met Thr Thr Asn His Ser Phe Met Cys Leu Ile Lys Tyr
                175                 180                 185

GGA CAT TTA AGA GTG AAT CAG ACC TTC AAC TGG AAT ACA ACC AAG CAA         1025
Gly His Leu Arg Val Asn Gln Thr Phe Asn Trp Asn Thr Thr Lys Gln
                190                 195                 200

GAG CAT TTT CCT GAT AAC CTG CTC CCA TCC TGG GCC ATT ACC TTA ATC         1073
Glu His Phe Pro Asp Asn Leu Leu Pro Ser Trp Ala Ile Thr Leu Ile
                205                 210                 215

TCA GTA AAT GGA ATT TTT GTG ATA TGC TGC CTG ACC TAC TGC TTT GCC         1121
Ser Val Asn Gly Ile Phe Val Ile Cys Cys Leu Thr Tyr Cys Phe Ala
220                 225                 230

CCA AGA TGC AGA GAG AGA AGG AGG AAT GAG AGA TTG AGA AGG GAA AGT         1169
Pro Arg Cys Arg Glu Arg Arg Arg Asn Glu Arg Leu Arg Arg Glu Ser
235                 240                 245                 250

GTA CGC CCT GTA    TAACAGTGTC CGCAGAAGCA AGGGGCTGAA AAGATCTGAA          1221
Val Arg Pro Val

GGTAGCCTCC GTCATCTCTT CTGGGATACA TGGATCGTGG GGATCATGAG GCATTCTTCC       1281

CTTAACAAAT TTAAGCTGTT TTACCCACTA CCTCACCTTC TTAAAAACCT CTTTCAGATT       1341

AAGCTGAACA GTTACAAGAT GGCTGGCATC CCTCTCCTTT CTCCCCATAT GCAATTTGCT       1401

TAATGTAACC TCTTCTTTTG CCATGTTTCC ATTCTGCCAT CTTGAATTGT CTTGTCAGCC       1461

AATTCATTAT CTATTAAACA CTAATTTGAG                                       1491

(2) INFORMATION FOR SEQ ID NO:23:

(i) SEQUENCE CHARACTERISTICS:
        (A) LENGTH: 288 amino acids
        (B) TYPE: amino acid
        (C) TOPOLOGY: linear (ii) MOLECULE TYPE: protein
        (A) DESCRIPTION: B cell activation antigen; natural ligand
            for CD28 T cell surface antigen; transmembrane protein (ix) FEATURE:
        (A) NAME/KEY: signal sequence
        (B) LOCATION: -34 to -1
        (C) IDENTIFICATION METHOD: amino terminal sequencing of
            soluble protein
        (D) OTHER INFORMATION: hydrophobic (ix) FEATURE:
        (A) NAME/KEY: extracellular domain
        (B) LOCATION: 1 to 208
        (C) IDENTIFICATION METHOD: similarity with known
            sequence (ix) FEATURE:
        (A) NAME/KEY: transmembrane domain
        (B) LOCATION: 209 to 235
        (C) IDENTIFICATION METHOD: similarity with known
            sequence (ix) FEATURE:
        (A) NAME/KEY: intracellular domain
        (B) LOCATION: 236 to 254
        (C) IDENTIFICATION METHOD: similarity with known
            sequence (ix) FEATURE:
        (A) NAME/KEY: N-linked glycosylation
        (B) LOCATION: 19 to 21
        (C) IDENTIFICATION METHOD: similarity with known
            sequence (ix) FEATURE:
```

-continued

```
        (A) NAME/KEY: N-linked glycosylation
        (B) LOCATION: 55 to 57
        (C) IDENTIFICATION METHOD: similarity with known
            sequence (ix) FEATURE:
        (A) NAME/KEY: N-linked glycosylation
        (B) LOCATION: 64 to 66
        (C) IDENTIFICATION METHOD: similarity with known
            sequence (ix) FEATURE:
        (A) NAME/KEY: N-linked glycosylation
        (B) LOCATION: 152 to 154
        (C) IDENTIFICATION METHOD: similarity with known
            sequence (ix) FEATURE:
        (A) NAME/KEY: N-linked glycosylation
        (B) LOCATION: 173 to 175
        (C) IDENTIFICATION METHOD: similarity with known
            sequence (ix) FEATURE:
        (A) NAME/KEY: N-linked glycosylation
        (B) LOCATION: 177 to 179
        (C) IDENTIFICATION METHOD: similarity with known
            sequence (ix) FEATURE:
        (A) NAME/KEY: N-linked glycosylation
        (B) LOCATION: 192 to 194
        (C) IDENTIFICATION METHOD: similarity with known
            sequence (ix) FEATURE:
        (A) NAME/KEY: N-linked glycosylation
        (B) LOCATION: 198 to 200
        (C) IDENTIFICATION METHOD: similarity with known
            sequence (ix) FEATURE:
        (A) NAME/KEY: Ig V-set domain
        (B) LOCATION: 1 to 104
        (C) IDENTIFICATION METHOD: similarity with known
            sequence (ix) FEATURE:
        (A) NAME/KEY: Ig C-set domain
        (B) LOCATION:  105 to 202
        (C) IDENTIFICATION METHOD: similarity with known
            sequence (x) PUBLICATION INFORMATION:
        (A) AUTHORS: FREEMAN, GORDON J.
            FREEDMAN, ARNOLD S.
            SEGIL, JEFFREY M.
            LEE, GRACE
            WHITMAN, JAMES F.
            NADLER, LEE M.
        (B) TITLE: B7, A New Member Of The Ig Superfamily With
            Unique Expression On Activated And Neoplastic B Cells
        (C) JOURNAL: The Journal of Immunology
        (D) VOLUME: 143
        (E) ISSUE: 8
        (F) PAGES: 2714-2722
        (G) DATE:  15-OCT-1989
        (H) RELEVANT RESIDUES IN SEQ ID NO:23: From -26 to 262

(xi) SEQUENCE DESCRIPTION: SEQ ID NO:23:

Met Gly His Thr Arg Arg Gln Gly Thr Ser Pro Ser Lys Cys Pro Tyr
            -30                 -25                 -20

Leu Asn Phe Phe Gln Leu Leu Val Leu Ala Gly Leu Ser His Phe Cys
            -15                 -10                 -5

Ser Gly Val Ile His Val Thr Lys Glu Val Lys Glu Val Ala Thr Leu
     -1   1               5                   10
```

```
Ser Cys Gly His Asn Val Ser Val Glu Glu Leu Ala Gln Thr Arg Ile
 15                  20                  25                  30

Tyr Trp Gln Lys Glu Lys Lys Met Val Leu Thr Met Met Ser Gly Asp
             35                  40                  45

Met Asn Ile Trp Pro Glu Tyr Lys Asn Arg Thr Ile Phe Asp Ile Thr
             50                  55                  60

Asn Asn Leu Ser Ile Val Ile Leu Ala Leu Arg Pro Ser Asp Glu Gly
             65                  70                  75

Thr Tyr Glu Cys Val Val Leu Lys Tyr Glu Lys Asp Ala Phe Lys Arg
     80                  85                  90

Glu His Leu Ala Glu Val Thr Leu Ser Val Lys Ala Asp Phe Pro Thr
 95                 100                 105                 110

Pro Ser Ile Ser Asp Phe Glu Ile Pro Thr Ser Asn Ile Arg Arg Ile
                115                 120                 125

Ile Cys Ser Thr Ser Gly Gly Phe Pro Glu Pro His Leu Ser Trp Leu
                130                 135                 140

Glu Asn Gly Glu Glu Leu Asn Ala Ile Asn Thr Thr Val Ser Gln Asp
            145                 150                 155

Pro Glu Thr Glu Leu Tyr Ala Val Ser Ser Lys Leu Asp Phe Asn Met
            160                 165                 170

Thr Thr Asn His Ser Phe Met Cys Leu Ile Lys Tyr Gly His Leu Arg
175                 180                 185                 190

Val Asn Gln Thr Phe Asn Trp Asn Thr Thr Lys Gln Glu His Phe Pro
                195                 200                 205

Asp Asn Leu Leu Pro Ser Trp Ala Ile Thr Leu Ile Ser Val Asn Gly
            210                 215                 220

Ile Phe Val Ile Cys Cys Leu Thr Tyr Cys Phe Ala Pro Arg Cys Arg
            225                 230                 235

Glu Arg Arg Arg Asn Glu Arg Leu Arg Arg Glu Ser Val Arg Pro Val
240                 245                 250
```

(2) INFORMATION FOR SEQ ID NO:24:

(i) SEQUENCE CHARACTERISTICS:
        (A) LENGTH: 1716 base pairs (B) TYPE: nucleic acid (C) STRANDEDNESS: double (D) TOPOLOGY: linear (ii) MOLECULE TYPE: cDNA to mRNA (iii) HYPOTHETICAL: no (vi) ORIGINAL SOURCE:
        (A) ORGANISM: Mus musculus (D) DEVELOPMENTAL STAGE: germ line (F) TISSUE TYPE: lymphoid (G) CELL TYPE: B lymphocyte (H) CELL LINE: 70Z and A20

(vii) IMMEDIATE SOURCE:
        (A) LIBRARY: cDNA in pCDM8 vector (B) CLONE: B7 #'s 1 and 29

5,942,607

55

56

-continued (ix) FEATURE:
(A) NAME/KEY: translated region
(B) LOCATION: 249 to 1166 bp
(C) IDENTIFICATION METHOD: similarity to other pattern (ix) FEATURE:
(A) NAME/KEY: Alternate ATG initiation codons
(B) LOCATION: 225 to 227 and 270 to 272
(C) IDENTIFICATION METHOD: similarity to other pattern (xi) SEQUENCE DESCRIPTION: SEQ ID NO:24:

```
GAGTTTTATA CCTCAATAGA CTCTTACTAG TTTCTCTTTT TCAGGTTGTG AAACTCAACC      60

TTCAAAGACA CTCTGTTCCA TTTCTGTGGA CTAATAGGAT CATCTTTAGC ATCTGCCGGG     120

TGGATGCCAT CCAGGCTTCT TTTTCTACAT CTCTGTTTCT CGATTTTTGT GAGCCTAGGA     180

GGTGCCTAAG CTCCATTGGC TCTAGATTCC TGGCTTTCCC CATCATGTTC TCCAAAGCAT     240

CTGAAGCT ATG GCT TGC AAT TGT CAG TTG ATG CAG GAT ACA CCA CTC CTC      290
         Met Ala Cys Asn Cys Gln Leu Met Gln Asp Thr Pro Leu Leu
             -35                 -30                 -25

AAG TTT CCA TGT CCA AGG CTC AAT CTT CTC TTT GTG CTG CTG ATT CGT       338
Lys Phe Pro Cys Pro Arg Leu Ile Leu Leu Phe Val Leu Leu Ile Arg
            -20                 -15                 -10

CTT TCA CAA GTG TCT TCA GAT GTT GAT GAA CAA CTG TCC AAG TCA GTG       386
Leu Ser Gln Val Ser Ser Asp Val Asp Glu Gln Leu Ser Lys Ser Val
         -5                  -1  1                   5

AAA GAT AAG GTA TTG CTG CCT TGC CGT TAC AAC TCT CCT CAT GAA GAT       434
Lys Asp Lys Val Leu Leu Pro Cys Arg Tyr Asn Ser Pro His Glu Asp
 10                  15                  20                  25

GAG TCT GAA GAC CGA ATC TAC TGG CAA AAA CAT GAC AAA GTG GTG CTG       482
Glu Ser Glu Asp Arg Ile Tyr Trp Gln Lys His Asp Lys Val Val Leu
                 30                  35                  40

TCT GTC ATT GCT GGG AAA CTA AAA GTG TGG CCC GAG TAT AAG AAC CGG       530
Ser Val Ile Ala Gly Lys Leu Lys Val Trp Pro Glu Tyr Lys Asn Arg
             45                  50                  55

ACT TTA TAT GAC AAC ACT ACC TAC TCT CTT ATC ATC CTG GGC CTG GTC       578
Thr Leu Tyr Asp Asn Thr Thr Tyr Ser Leu Ile Ile Leu Gly Leu Val
         60                  65                  70

CTT TCA GAC CGG GGC ACA TAC AGC TGT GTC GTT CAA AAG AAG GAA AGA       626
Leu Ser Asp Arg Gly Thr Tyr Ser Cys Val Val Gln Lys Lys Glu Arg
     75                  80                  85

GGA ACG TAT GAA GTT AAA CAC TTG GCT TTA GTA AAG TTG TCC ATC AAA       674
Gly Thr Tyr Glu Val Lys His Leu Ala Leu Val Lys Leu Ser Ile Lys
 90                  95                 100                 105

GCT GAC TTC TCT ACC CCC AAC ATA ACT GAG TCT GGA AAC CCA TCT GCA       722
Ala Asp Phe Ser Thr Pro Asn Ile Thr Glu Ser Gly Asn Pro Ser Ala
                110                 115                 120

GAC ACT AAA AGG ATT ACC TGC TTT GCT TCC GGG GGT TTC CCA AAG CCT       770
Asp Thr Lys Arg Ile Thr Cys Phe Ala Ser Gly Gly Phe Pro Lys Pro
            125                 130                 135

CGC TTC TCT TGG TTG GAA AAT GGA AGA GAA TTA CCT GGC ATC AAT ACG       818
Arg Phe Ser Trp Leu Glu Asn Gly Arg Glu Leu Pro Gly Ile Asn Thr
        140                 145                 150

ACA ATT TCC CAG GAT CCT GAA TCT GAA TTG TAC ACC ATT AGT AGC CAA       866
Thr Ile Ser Gln Asp Pro Glu Ser Glu Leu Tyr Thr Ile Ser Ser Gln
    155                 160                 165

CTA GAT TTC AAT ACG ACT CGC AAC CAC ACC ATT AAG TGT CTC ATT AAA       914
Leu Asp Phe Asn Thr Thr Arg Asn His Thr Ile Lys Cys Leu Ile Lys
```

```
                        170                 175                 180                 185
TAT GGA GAT GCT CAC GTG TCA GAG GAC TTC ACC TGG GAA AAA CCC CCA          962
Tyr Gly Asp Ala His Val Ser Glu Asp Phe Thr Trp Glu Lys Pro Pro
                190                 195                 200

GAA GAC CCT CCT GAT AGC AAG AAC ACA CTT GTG CTC TTT GGG GCA GGA          1010
Glu Asp Pro Pro Asp Ser Lys Asn Thr Leu Val Leu Phe Gly Ala Gly
                205                 210                 215

TTC GGC GCA GTA ATA ACA GTC GTC GTC ATC GTT GTC ATC ATC AAA TGC          1058
Phe Gly Ala Val Ile Thr Val Val Val Ile Val Val Ile Ile Lys Cys
                220                 225                 230

TTC TGT AAG CAC AGA AGC TGT TTC AGA AGA AAT GAG GCA AGC AGA GAA          1106
Phe Cys Lys His Arg Ser Cys Phe Arg Arg Asn Glu Ala Ser Arg Glu
        235                 240                 245

ACA AAC AAC AGC CTT ACC TTC GGG CCT GAA GAA GCA TTA GCT GAA CAG          1154
Thr Asn Asn Ser Leu Thr Phe Gly Pro Glu Glu Ala Leu Ala Glu Gln
250                 255                 260                 265

ACC GTC TTC CTT TAGTTCTTCT CTGTCCATGT GGGATACATG GTATTATGTG              1206
Thr Val Phe Leu

GCTCATGAGG TACAATCTTT CTTTCAGCAC CGTGCTAGCT GATCTTTCGG ACAACTTGAC        1266

ACAAGATAGA GTTAACTGGG AAGAGAAAGC CTTGAATGAG GATTTCTTTC CATCAGGAAG        1326

CTACGGGCAA GTTTGCTGGG CCTTTGATTG CTTGATGACT GAAGTGGAAA GGCTGAGCCC        1386

ACTGTGGGTG GTGCTAGCCC TGGGCAGGGG CAGGTGACCC TGGGTGGTAT AAGAAAAAGA       1446

GCTGTCACTA AAAGGAGAGG TGCCTAGTCT TACTGCAACT TGATATGTCA TGTTTGGTTG        1506

GTGTCTGTGG GAGGCCTGCC CTTTTCTGAA GAGAAGTGGT GGGAGAGTGG ATGGGGTGGG       1566

GGCAGAGGAA AAGTGGGGGA GAGGGCCTGG GAGGAGAGGA GGGAGGGGGA CGGGGTGGGG       1626

GTGGGGAAAA CTATGGTTGG GATGTAAAAA CGGATAATAA TATAAATATT AAATAAAAAG       1686

AGAGTATTGA GCAAAAAAAA AAAAAAAAA                                         1716
```

(2) INFORMATION FOR SEQ ID NO:25:

(i) SEQUENCE CHARACTERISTICS:
        (A) LENGTH: 306 amino acids (B) TYPE: amino acid (C) TOPOLOGY: linear (ii) MOLECULE TYPE: protein
        (A) DESCRIPTION: B lymphocyte activation antigen; Ig superfamily member; T cell costimulatory signal
            via activation of CD28 pathways, binds to CD28+
            T cells, transmembrane protein (ix) FEATURE:
        (A) NAME/KEY: signal sequence (B) LOCATION: -37 to -1

(C) IDENTIFICATION METHOD: similarity with known sequence
        (D) OTHER INFORMATION: hydrophobic (ix) FEATURE:
        (A) NAME/KEY: extracellular domain
        (B) LOCATION: 1 to 210
        (C) IDENTIFICATION METHOD: similarity with known
            sequence (ix) FEATURE:
        (A) NAME/KEY: transmembrane domain (B) LOCATION: 211 to 235
          (C) IDENTIFICATION METHOD: similarity with known
              sequence (ix) FEATURE:
          (A) NAME/KEY: intracellular (cytoplasmic) domain
          (B) LOCATION: 236 to 269
          (C) IDENTIFICATION METHOD: similarity with known
              sequence (ix) FEATURE:
          (A) NAME/KEY: Ig V-set domain
          (B) LOCATION: 1 to 105
          (C) IDENTIFICATION METHOD: similarity with known
              sequence (ix) FEATURE:
          (A) NAME/KEY: Ig C-set domain
          (B) LOCATION:  106 to 199
          (C) IDENTIFICATION METHOD: similarity with known
              sequence (x) PUBLICATION INFORMATION:
          (A) AUTHORS: FREEMAN, GORDON J.
              GRAY, GARY S.
              GIMMI, CLAUDE D.
              LOMBARD, DAVID B.
              ZHOU, LIANG-JI
              WHITE, MICHAEL
              FINGEROTH, JOYCE D.
              GRIBBEN, JOHN G.
              NADLER, LEE M.
          (B) TITLE: Structure, Expression, and T Cell Costimulatory
              Activity Of The Murine Homologue Of The Human B
              Lymphocyte Activation Antigen B7
          (C) JOURNAL: Journal of Experimental Medicine
          (D) VOLUME:
          (E) ISSUE:
          (F) PAGES:
          (G) DATE: IN PRESS
          (H) RELEVANT RESIDUES IN SEQ ID NO:25: From -37 to 269

(xi) SEQUENCE DESCRIPTION: SEQ ID NO:25:

Met Ala Cys Asn Cys Gln Leu Met Gln Asp Thr Pro Leu Leu Lys Phe
    -35                 -30                 -25

Pro Cys Pro Arg Leu Ile Leu Leu Phe Val Leu Leu Ile Arg Leu Ser
    -20                 -15                 -10

Gln Val Ser Ser Asp Val Asp Glu Gln Leu Ser Lys Ser Val Lys Asp
 -5              -1   1               5                  10

Lys Val Leu Leu Pro Cys Arg Tyr Asn Ser Pro His Glu Asp Glu Ser
                 15                  20                  25

Glu Asp Arg Ile Tyr Trp Gln Lys His Asp Lys Val Val Leu Ser Val
             30                  35                  40

Ile Ala Gly Lys Leu Lys Val Trp Pro Glu Tyr Lys Asn Arg Thr Leu
             45                  50                  55

Tyr Asp Asn Thr Thr Tyr Ser Leu Ile Ile Leu Gly Leu Val Leu Ser
 60                  65                  70                  75

Asp Arg Gly Thr Tyr Ser Cys Val Val Gln Lys Lys Glu Arg Gly Thr
                 80                  85                  90

Tyr Gly Val Lys His Leu Ala Leu Val Lys Leu Ser Ile Lys Ala Asp
             95                  100                 105

Phe Ser Thr Pro Asn Ile Thr Glu Ser Gly Asn Pro Ser Ala Asp Thr
        110                 115                 120

Lys Arg Ile Thr Cys Phe Ala Ser Gly Gly Phe Pro Lys Pro Arg Phe
        125                 130                 135

Ser Trp Leu Glu Asn Gly Arg Glu Leu Pro Gly Ile Asn Thr Thr Ile
140                 145                 150                 155

```
Ser Gln Asp Pro Glu Ser Glu Leu Tyr Thr Ile Ser Ser Gln Leu Asp
            160                 165                 170

Phe Asn Thr Thr Arg Asn His Thr Ile Lys Cys Leu Ile Lys Tyr Gly
            175                 180             185

Asp Ala His Val Ser Glu Asp Phe Thr Trp Glu Lys Pro Pro Glu Asp
        190                 195                 200

Pro Pro Asp Ser Lys Asn Thr Leu Val Leu Phe Gly Ala Gly Phe Gly
        205                 210                 215

Ala Val Ile Thr Val Val Val Ile Val Val Ile Ile Lys Cys Phe Cys
220                 225                 230                 235

Lys His Arg Ser Cys Phe Arg Arg Asn Glu Ala Ser Arg Glu Thr Asn
                240                 245                 250

Asn Ser Leu Thr Phe Gly Pro Glu Glu Ala Leu Ala Glu Gln Thr Val
            255                 260                 265

Phe Leu
```